United States Patent [19]

Holly et al.

[11] Patent Number: 5,541,085
[45] Date of Patent: Jul. 30, 1996

[54] METHOD FOR PREPARING ORPHAN RECEPTOR LIGANDS

[75] Inventors: Richard D. Holly; Steven K. Burkhead, both of Seattle, Wash.

[73] Assignee: ZymoGenetics, Inc., Seattle, Wash.

[21] Appl. No.: 250,859

[22] Filed: May 27, 1994

Related U.S. Application Data

[63] Continuation-in-part of Ser. No. 196,025, Feb. 14, 1994, abandoned.

[51] Int. Cl.$^6$ .............................. C12N 15/12; C12N 15/19
[52] U.S. Cl. ......................... 435/69.1; 435/6; 435/172.3; 435/69.5
[58] Field of Search ..................................... 436/501, 517; 435/6, 7.21, 69.1, 172.3, 69.5

[56] References Cited

U.S. PATENT DOCUMENTS 5,348,872  9/1994  Lin et al. .............................. 435/172.1

FOREIGN PATENT DOCUMENTS 9200091  1/1992  WIPO .

OTHER PUBLICATIONS

Ferro, Jr. et al., *J. Biol. Chem.* 268: 5741–5747, 1993.
Palacios et al., *Cell*, 41: 727–734, 1985.
Methia et al., *Blood* 82: 1395–1401, 1993.
Vigon et al., *Proc. Natl. Acad. Sci USA* 89: 5640–5644, 1992.
Skoda et al., *EMBO J.* 12: 2645–2653, 1993.
Wilks et al., *Growth Factors* 2: 31–42, 1989.
Stocking et al., *Growth Factors* 8: 197–209, 1993.
Stocking et al., *Cell* 53: 869–879, 1988.
Dexter et al., *J. Exp. Med.* 152: 1036–1047, 1980.
Avanzi et al., *J. Cell. Physiol.* 145: 458–464, 1990.
Collins et al., *J. Cell. Physiol.* 137: 293–298, 1988.

*Primary Examiner*—John Ulm
*Attorney, Agent, or Firm*—Gary E. Parker; Debra K. Leith; Deborah A. Sawislak

[57] ABSTRACT

Methods for obtaining cells that produce a ligand for an orphan receptor and methods for preparing polynucleotide molecules that encode ligands for orphan receptors are disclosed. The methods utilize growth factor-dependent parent cells that are transfected with a DNA construct encoding an orphan receptor. The transfected cells are exposed to mutagenizing conditions, and the mutagenized cells are cultured under conditions in which cell survival is dependent upon autocrine growth factor production. Progeny cells are recovered and screened to identify those that produce a ligand for the orphan receptor. Polynucleotide molecules encoding the ligand can be prepared from the identified cells.

14 Claims, 2 Drawing Sheets

| Receptor Family | Receptor Structure | | Ligand |
|---|---|---|---|
| | Extracellular | Intracellular | |
| 1. Immunoglobulin | | | CSF-1 |
| | | | IL-1 |
| 2. Hybrid | | | G-CSF |
| | | | IL-6 |
| 3. Hematopoietin | | | EPO |
| | | | IL-3 |
| 4. TNF-Receptor | | | TNF (p80) |
| | | | TNF (p60) |
| 5. Other | | | IL-2 (α subunit) |
| | | | IFN-γ |

Legend:
-  Immunoglobulin Domain
-  Protein Kinase Domain
-  Hematopoietin Domain
-  TNF Domain
- ⊢——⊣ 100 Amino Acids

METHOD FOR PREPARING ORPHAN RECEPTOR LIGANDS

CROSS-REFERENCE TO RELATED APPLICATION

The present application is a continuation-in-part of Ser. No. 08/196,025, filed Feb. 14, 1994, now abandoned, which is incorporated herein by reference.

BACKGROUND OF THE INVENTION

Proliferation and differentiation of cells of multicellular organisms are controlled by hormones and polypeptide growth factors. These diffusable molecules allow cells to communicate with each other and act in concert to form organs and repair damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signalling pathways within the cell, such as second messenger systems. Other classes of receptors are soluble molecules, such as the transcription factors.

The study of receptor-ligand interactions has revealed a great deal of information about how cells respond to external stimuli. This knowledge has led to the development of therapeutically important compounds, such as erythropoietin, the colony stimulating factors and PDGF. Nevertheless, many molecules that control cell growth and development are probably yet to be discovered. In some instances, receptors are known, but their ligands remain to be identified. Discovery of new hormones and growth factors would be aided by the provision of new molecular tools, including receptors, ligands and growth factor-dependent cells. The present invention provides such tools as well as other, related advantages.

SUMMARY OF THE INVENTION

It is an object of the present invention to provide methods for identifying and isolating ligands for orphan receptors.

It is a further object of the present invention to provide methods for cloning polynucleotide molecules encoding ligands for orphan receptors.

It is yet another object of the present invention to provide cell lines that produce ligands for orphan receptors.

Within one aspect of the invention, a method for obtaining cells that produce a ligand for an orphan receptor is provided. Broadly stated, the method comprises the steps of (a) providing parent cells, wherein growth of the parent cells is dependent upon an exogenous growth factor; (b) transfecting the parent cells with a DNA construct encoding an orphan receptor to produce transfected cells expressing the orphan receptor encoded by the DNA construct; (c) exposing the transfected cells to mutagenizing conditions to produce mutagenized cells; (d) culturing the mutagenized cells under conditions in which cell survival is dependent upon autocrine growth factor production; (e) recovering progeny cells that survive the culturing step; and (f) screening the progeny cells to identify cells that produce a ligand for the orphan receptor. Within one embodiment, the screening step comprises culturing the progeny cells in the presence of an antibody to a known growth factor. Within an alternative embodiment, the screening step comprises culturing the progeny cells in the presence of a soluble form of the orphan receptor. Within another embodiment, the screening step comprises assaying media conditioned by said progeny cells for growth-promoting activity on said parent cells. Within a preferred embodiment, the parent cells do not express detectable levels of the orphan receptor. Within another preferred embodiment, the parent cells are myeloid or lymphoid progenitor cells.

Within another aspect of the invention, a method for preparing a polynucleotide molecule that encodes a ligand for an orphan receptor is provided. The method comprises the steps of (a) providing parent cells, wherein growth of the cells is dependent upon an exogenous growth factor; (b) transfecting the parent cells with a DNA construct encoding an orphan receptor to produce transfected cells expressing the orphan receptor encoded by the DNA construct; (c) exposing the transfected cells to mutagenizing conditions to produce mutagenized cells; (d) culturing the mutagenized cells under conditions in which cell survival is dependent upon autocrine growth factor production; (e) recovering progeny cells that survive the culturing step; (f) screening the progeny cells to identify cells that produce a ligand for the orphan receptor; and (g) preparing polynucleotide molecules encoding the ligand from the identified cells. Polynucleotides that can be prepared accoding to this method include cDNA, genomic DNA and mRNA.

These and other aspects of the invention will become evident upon reference to the following detailed description and the attached drawing.

DETAILED DESCRIPTION OF THE INVENTION

The present invention provides materials and methods that are useful for identifying, isolating and preparing ligands for receptors and polynucleotide molecules encoding those ligands. These materials and methods are particularly useful when the receptor of interest is an "orphan" receptor, that is a receptor for which the identity of the natural ligand is unknown. The present invention thus provides useful tools for identifying, isolating and cloning new growth factors that are useful in, inter alia, cell culturing in research and industrial settings, studies of cell physiology and metabolism, and therapeutic intervention in animals including humans.

The term "receptor" is used herein to denote a cell-associated protein that binds to a bioactive molecule (the "ligand") and mediates the effect of the ligand on the cell. Receptors are characterized by a multi-domain structure comprising a ligand-binding domain and an effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Receptors can be membrane bound, cytosolic or nuclear; monomeric (e.g. thyroid stimulating hormone receptor, beta-adrenergic receptor) or multimeric (e.g. PDGF receptor, growth hormone receptor, IL-3 receptor, GM-CSF receptor, G-CSF receptor, erythropoietin receptor and IL-6 receptor).

Receptors are classified into families and superfamilies on the basis of conserved structural features. It is generally believed that under selective pressure for organisms to acquire new biological functions, new receptor family members arose from duplication of existing receptor genes leading to the existence of multi-gene families. Family members thus contain vestiges of the ancestral gene, and these characteristic features can be exploited in the isolation and identification of additional family members.

Three of the most well-known receptor superfamilies are the cytokine receptor superfamily, the seven transmembrane domain (7-TMD) receptor superfamily, and the steroid receptor superfamily. Table 1 provides a partial listing of members of these three receptor superfamilies.

Figure 1:
FIG. 1 illustrates the common structural features of five related families of cytokine receptors.
Figure 1:
Figure 1:
Figure 1:
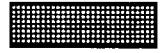

Many cytokine receptors can be placed into one of five related families on the basis of the structural features shown in FIG. 1. All five families are characterized by the presence of an extracellular ligand binding domain and an intracellular domain that are separated by a single transmembrane sequence. Cytokine receptor structure has been reviewed by Urdal, *Ann. Reports Med. Chem.* 26:221–228, 1991 and Cosman, *Cytokine* 5:95–106, 1993.

The 7-TMD receptors are a functionally diverse group encoded by a large gene superfamily. Two characteristic features of this receptor superfamily are the presence of seven helical transmembrane domains and a cytoplasmic domain, the latter of which is believed to be responsible for coupling the receptor to G proteins. This superfamily has been reviewed by Lameh et al., *Pharm Res.* 7:1213–1221, 1990; Hargrave, *Curr. Opin. Struct. Biol.* 1:575–581, 1991; and Probst et al., *DNA and Cell Biol.* 11:1–20, 1992.

The steroid receptors may be viewed as ligand-dependent transcription factors. The majority of these receptors appear to contain three domains: a variable, amino-terminal domain; a highly conserved, DNA-binding domain; and a moderately conserved, carboxyl-terminal, ligand-binding domain. The steroid hormone receptor superfamily has been reviewed by Power et al., *TiPS* 13:318–323, 1992; Parker, *Curr. Opin. Cell Biol.* 5:499–504, 1993; and McDonnell et al., *Bio/Technology* 11:1256–1261, 1993. In addition to the known steroid receptors, at least 40 orphan members of this superfamily have been identified (Laudet et al., *EMBO J.* 11:1003–1013, 1992 and Power et al., ibid.).

Table 1

Cytokine superfamily
  Immunoglobulin family
    CSF-1 receptor
    MGF receptor
    IL-1 receptor
    PDGF receptor
  Hybrid family
    G-CSF receptor
    IL-6 receptor
  Hematopoietin family
    erythropoietin receptor
    IL-2 receptor β-subunit
    IL-3 receptor
    IL-4 receptor
    IL-5 receptor Table 1, continued IL-7 receptor
    IL-9 receptor
    GM-CSF receptor α-subunit
    GM-CSF receptor β-subunit
    IL-6 receptor
    growth hormone receptor
  TNF receptor
    TNF (p80) receptor
    TNF (p60) receptor
  Other
    IL-2 receptor α-subunit
    IFN-γ receptor
7-TMD superfamily
  m1 muscarinic acetylcholine receptor
  m2 muscarinic acetylcholine receptor
  m3 muscarinic acetylcholine receptor
  m4 muscarinic acetylcholine receptor
  m5 muscarinic acetylcholine receptor
  beta 1 adrenergic receptor
  beta 2 adrenergic receptor
  beta 3 adrenergic receptor
  alpha 1 adrenergic receptor
  alpha 2A adrenergic receptor
  alpha 2B adrenergic receptor
  alpha 2-C4 adrenergic receptor
  dopamine D1 receptor
  dopamine D2 receptor
  dopamine D3 receptor
  dopamine D4 receptor
  dopamine D5 receptor
  thrombin receptor
  thromboxane receptor
  FSH receptor
  cannabinoid receptor
  gonadotropin receptor Table 1, continued thyrotropin receptor
  calcitonin receptor
  parathyroid hormone receptor
Steroid superfamily
  vitamin D receptor
  glucocorticoid receptor
  mineralocorticoid receptor
  progesterone receptor
  androgen receptor
  estrogen receptor
  retinoic acid receptor
  retinoid X receptor Receptors are also classified on the basis of common functions. Table 2 presents a listing of receptor families grouped according to function. Each tyrosine kinase family is represented in Table 2 by a prototypical receptor. See Ullrich et al., *Nature* 308:418–425, 1984; Ullrich et al., *Nature* 313:756–761, 1985; Yaden et al., *Nature* 323:226–232; Hirai et al., *Science* 238:1717–1720, 1987;

Sanchez-Madrid et al., *Proc. Natl. Acad. Sci. USA* 79:7489–7493, 1982; Takeichi, *Science* 251:1451–1455, 1991; Takeichi, *Ann. Rev. Biochem.* 59:237–252, 1990; and Cunningham et al., *Science* 236:799–806, 1987.

Table 2

Tyrosine kinase receptors
EGF receptor
insulin receptor
PDGF receptor
EPH receptor
Cell adhesion receptors
leukointegrins
cadherin receptors
immunoglobulin-like receptors The present invention is based upon a novel process of transfection, mutagenesis and selection that is used to obtain cells, the growth of which is dependent upon an unknown ligand, which produce the ligand. The cells are thus able to grow in the absence of exogenous ligand. Cells obtained in this way can be used, for example, as sources of isolated ligand or nucleic acid molecules encoding the ligand.

The process begins with a cultured parent cell that is dependent on an exogenous growth factor for its proliferation. Suitable cells include animal cells that can be grown in culture. Cultured mammalian cells are preferred. The cells are transfected to produce an orphan receptor. Within a preferred embodiment, the untransfected parent cell does not express detectable levels of the orphan receptor, thereby providing a matched pair of cells with and without the receptor. Many orphan receptors have been identified, and it is anticipated that many more will be found as knowledge of the molecular biology of cells increases. Known orphan receptors include the nuclear receptors COUP-TF1/EAR3, COUP-TF2/ARP-1, EAR-1, EAR-2, TR-2, PPAR1, HNF-4, ERR-1, ERR-2, NGFI-B/Nur77, ELP/SF-1 and, prior to studies disclosed herein, MPL (see reviews by Parker, ibid. and Power et al., ibid.). A large number of orphan receptors have been identified in the EPH family (Hirai et al., ibid., incorporated herein by reference). HER3 and HER4 (Plowman et al., *Proc. Natl. Acad. Sci. USA* 90:1746–1750, 1993, incorporated herein by reference) are orphan receptors in the epidermal growth factor receptor family, which may be overexpressed in a number of carcinomas. ILA is a newly identified member of the human nerve growth factor/tumor necrosis factor receptor family (Schwarz et al., *Gene* 134:295–298, 1993, incorporated herein by reference). An orphan receptor in the insulin receptor family, designated insulin receptor-related receptor (IRRR) is disclosed by Shier et al. (*J. Biol. Chem.* 264: 14606–14608, 1989, which is incorporated herein by reference). IRRR is a transmembrane tyrosine kinase. In addition, a number of orphan tyrosine kinase-type receptors have been found in Drosophila (reviewed by Perrimon, *Curr. Opin. Cell Biol.* 6:260–266, 1994, which is incorporated herein by reference). Drosophila orphan receptors are of interest because they present the opportunity for genetic, as well as biochemical, analysis. Identification of Drosophila ligands followed by cloning by homology provides a method for obtaining human or other animal counterparts to the Drosophila ligands.

The parent cells are transfected with a DNA construct encoding the orphan receptor. Such a DNA construct will typically be in the form of a plasmid or virus-derived expression vector. Methods for constructing expression vectors and transfecting cultured cells are known in the art. See, for example, Levinson et al., U.S. Pat. No. 4,713,339; Hagen et al., U.S. Pat. No. 4,784,950; Palmiter et al., U.S. Pat. No. 4,579,821 and Ringold, U.S. Pat. No. 4,656,134, which are incorporated herein by reference in their entirety. In general, a DNA segment encoding the orphan receptor of interest is joined to expression control sequences in a plasmid or viral vector that may comprise, in addition, one or more origins of replication, one or more selectable markers, enhancers, splice signals or other elements. The DNA construct is inserted into the host cell using conventional methods. It is preferred to use established cell lines, although primary cultures may also be used.

As noted above, the cell is one in which growth is dependent upon an exogenous growth factor. As used herein, the term "growth factor" denotes a polypeptide that stimulates proliferation of a cell, the activity of which is mediated by a cell-surface receptor. Examples of growth factors include the interleukins and colony stimulating factors. Growth factor-dependent myeloid and lymphoid progenitor cells are preferred. These are cells that give rise to differentiated blood cells and that are found in hematopoietic tissue such as bone marrow, spleen and fetal liver. Myeloid and lymphoid precursors are also found in peripheral blood after treatment of an animal with cytokines. Preferred growth factor-dependent cell lines that can be transfected to express orphan receptors include BaF3 (Palacios and Steinmetz, *Cell* 41: 727–734, 1985; Mathey-Prevot et al., *Mol. Cell. Biol.* 6: 4133–4135, 1986), FDC-P1 (Hapel et al., *Blood* 64: 786–790, 1984), and MO7e (Kiss et al., *Leukemia* 7: 235–240, 1993). Additional growth factor-dependent cell lines are known and available in the art and are disclosed by, for example, Greenberger et al., *Proc. Natl. Acad. Sci. USA* 80:2931–2935, 1983; Dexter et al., *J. Exp. Med.* 152:1036–1047, 1980; and Greenberger et al., *Virology* 105:425–435, 1980. In addition, growth factor-dependent cell lines can be established according to published methods (e.g. Greenberger et al., *Leukemia Res.* 8: 363–375, 1984; Dexter et al., in Baum et al. Eds., *Experimental Hematology Today,* 8th Ann. Mtg. Int. Soc. Exp. Hematol. 1979, 145–156, 1980). In a typical procedure, cells are removed from the tissue of interest (e.g. bone marrow, spleen, fetal liver) and cultured in a conventional, serum-supplemented medium, such as RPMI 1640 supplemented with 10% fetal bovine serum (FBS), 15% horse serum and $10^{-6}$M hydrocortisone. At one- to two-week intervals non-adherent cells are harvested, and the cultures are fed fresh medium. The harvested, non-adherent cells are washed and cultured in medium with an added source of growth factor (e.g. RPMI 1640+10% FBS+5–20% WEHI-3 conditioned medium as a source of IL-3). These cells are fed fresh medium at one- to two-week intervals and expanded as the culture grows. After several weeks to several months, individual clones are isolated by plating the cells onto semi-solid medium (e.g. medium containing methylcellulose) or by limiting dilution. Factor dependence of the clones is confirmed by culturing individual clones in the absence of the growth factor. Retroviral infection or chemical mutagenesis can be used to obtain a higher frequency of growth factor-dependent cells.

The orphan receptor-expressing cell is mutagenized to produce a mutant cell. Methods for mutagenizing cells are known in the art and include chemical treatment, exposure to ultraviolet light, exposure to x-rays, and retroviral insertional mutagenesis. Chemical mutagenesis, such as by exposure to ethyl methanesulfonate (EMS), is preferred. Other useful chemical mutagens include nitrosoguanidine, 5-bromouracil, acridine, and aflatoxin. The proportion of mutagenized cells obtained is a function of the strength or amount of mutagenizing agent to which the cells are exposed. A low level of mutagen produces a small proportion of mutant cells. Higher levels of mutagen produce a higher proportion of mutant cells, but also kill more cells. It is therefore necessary to balance mutagenesis with killing so that a reasonable number of mutant cells is obtained. Balancing is generally done empirically by exposing cells to different conditions to establish a killing curve. In general, the cells are exposed to mutagenizing conditions and cultured for one day, after which they are tested for viability according to standard assay methods. Within the present invention, it is preferred to use a level of mutagenesis that results in 20–50% mortality, although one skilled in the art will recognize that this value can be adjusted as necessary, for example if working with a very large number of cells.

The mutagenesis procedure provides a third cell to complement the matched pair of cells with and without the receptor disclosed above. This set of three cells is a valuable set of tools for use in cloning polynucleotide molecules encoding orphan receptors or their ligands, and for use in related processes.

The mutagenized cells are cultured under conditions in which cell survival is dependent upon autocrine growth factor production, that is in the absence of an exogenous growth factor required by the parent cell, to obtain progeny cells. This selection step is very sensitive because only cells that, through mutagenesis, produce a factor required for their growth or have otherwise become growth factor independent will survive. It is therefore preferred to mutagenize a large number (typically $1–5 \times 10^7$) of cells due to the rarity of such mutagenic events. Methods for culturing cells are well known in the art. Although the particular conditions will be determined by the specific needs of the particular cell employed, in general the cells will be cultured in a conventional medium containing carbon and nitrogen sources, minerals, and other nutrients and under suitable conditions of temperature and atmosphere. For example, mammalian cell lines are typically cultured in a buffered cell culture medium containing a carbon source, a nitrogen source, salts, vitamins, antibiotics, amino acids, other metabolites (e.g. nucleosides, tricarboxylic acid intermediates and lipids) and serum at a temperature of about 37° C. in a 5% $CO_2$ atmosphere. Determination of conditions suitable for the culture of a particular cell is within the level of ordinary skill in the art. See, in general, Jacoby and Pastan, eds., *Meth. Enzymol.* vol LVIII, Academic Press, 1979 and Freshney, *Culture of Animal Cells: A Manual of Basic Technique*, 3rd ed., Wiley-Liss, 1994, which are incorporated herein by reference. Cell culture media are available from commercial suppliers such as GIBCO BRL (Gaithersburg, Md.) and JRH Bioscience (Lexena, Kans.), or may be prepared according to published recipes (see, e.g., catalogs of the American Type Culture Collection, Rockville, Md.).

Within a preferred embodiment, the cell is cultured in the presence of the exogenous growth factor before it is cultured in the absence of the growth factor. In general, the cells are cultured in the presence of growth factor for about one to seven days prior to being switched to a growth factor-free medium. Within a particularly preferred embodiment, the cells are allowed to recover for about 24 hours in the presence of exogenous growth factor, then plated at 50,000–100,000 cells per well in 24-well culture plates using growth factor-free culture medium. While not wishing to be bound by theory, it is believed that this recovery period allows time for phenotypic expression of the mutagenized gene(s), thereby increasing the liklihood that viable mutagenized cells will be recovered.

The progeny cells are then screened to identify cells that produce a ligand for said cell-surface receptor. This screening step differentiates ligand-producing cells from cells that have undergone other mutagenic events that could be responsible for the apparent autocrine growth stimulation. In general, assays are performed by testing media conditioned by the progeny cells for growth-promoting activity. As used herein, the term "media conditioned by the progeny cells" includes fractions or concentrates of conditioned media. Those skilled in the art will recognize that several types of assays can be used to rule out the presence of unwanted activities and confirm the presence of the activity of interest. Preferred assays for use within the present invention include activity assays using different target cells and neutralization assays. Activity assays are preferred as the primary screen. In a preferred embodiment, progeny cell-conditioned media is assayed for stimulatory activity on transfected and untransfected parent cells. Stimulatory activity specific for the transfected cells indicates that the ligand for the orphan receptor may be present in the conditioned media. Neutralization assays include assays employing antibodies against potential ligands or soluble forms of the cell-surface receptor of interest. In one embodiment, media conditioned by progeny cells is applied to the transfected parent cells that express the orphan receptor. Antibodies against known growth factors are then added to the media singly and in various combinations. Inhibition of cell growth by one or more of the antibodies indicates that the progeny cells are producing a known ligand. In another embodiment, the transfected parent cells are cultured in progeny cell conditioned media, and a soluble form of the orphan receptor is added to the culture. Inhibition of growth by the soluble receptor indicates that the ligand of interest is being produced by the progeny cells. Those skilled in the art will recognized that variations on these assays can also be employed, such as characterizing the activity by adding antibodies or soluble receptor to the cultured progeny cells.

Within the procedures disclosed above, viable cells are identified by visual inspection of the cultures and/or by viability assay. Many suitable viability assays are known in the art, and include assays for metabolism of a dye such as 3-(4,5-dimethylthiazol-2-yl)-2,5-diphenyl tetrazolium bromide (Mosman, *J. Immunol. Meth.* 65: 55–63, 1983); 3,(4,5 dimethylthiazol-2yl)-5-3-carboxymethoxyphenyl-2H-tetrazolium; 2,3-bis(2-methoxy-4-nitro-5-sulfophenyl)-5-[(phenylamino)carbonyl]-2H-tetrazolium hydroxide; and cyanoditolyl-tetrazolium chloride (which are commercially available from Polysciences, Inc., Warrington, Pa.); mitogenesis assays, such as measurement of incorporation of $^3$H-thymidine; dye exclusion assays using, for example, napthalene black or trypan blue; dye uptake using diacetyl fluorescein; and chromium release. See, in general, Freshney, *Culture of Animal Cells: A Manual of Basic Technique*, 3rd ed., Wiley-Liss, 1994, which is incorporated herein by reference.

Cells producing the ligand for the orphan receptor are a source of polynucleotide molecules that can be used to produce large quantities of the ligand. Useful polynucleotide molecules in this regard include mRNA, cDNA and genomic DNA. For recombinant protein production, cDNA is preferred. Methods for preparing these polynucleotide molecules are well known in the art. See, for example, Sambrook et al., eds, *Molecular Cloning: A Laboratory Manual*, Second Edition, Cold Spring Harbor Laboratory Press, 1989; Mullis et al., U.S. Pat. No. 4,683,195; and Chirgwin et al., *Biochemistry* 18: 52–94, 1979. Vectors, enzymes, and other reagents for use in isolation and cloning of polynucleotide molecules are readily available from commercial suppliers.

Isolated polynucleotide molecules encoding ligands for orphan receptors are useful in the production of polypeptide ligands through the techniques of genetic engineering. In general, the polynucleotide molecule is joined to expression control sequences in a plasmid or viral vector that may comprise, in addition, one or more origins of replication, one or more selectable markers, enhancers, splice signals or other elements. The vector is inserted into a host cell, which is in turn cultured under suitable conditions so that the ligand is produced. Methods for vector construction, host cell transfection and protein production are well known in the art. See, for example, Sambrook et al., ibid; Welch et al., U.S. Pat. No. 5,037,743; Kawasaki, U.S. Pat. No. 4,599,311; Kawasaki et al., U.S. Pat. No. 4,931,373; McKnight et al., U.S. Pat. No. 4,935,349; Levinson et al., U.S. Pat. No. 4,713,339; Hagen et al., U.S. Pat. No. 4,784,950; Palmiter et al., U.S. Pat. No. 4,579,821 and Ringold, U.S. Pat. No. 4,656,134, which are incorporated herein by reference in their entirety.

The invention is further illustrated by the following non-limiting examples.

EXAMPLES

Example I

Isolation of human MPL receptor cDNAs

Human MPL-P and MPL-K receptor isoform encoding cDNAs were isolated from human erythroid leukemic (HEL) cells (Martin and Papayannopoulu, *Science* 216: 1233–1235, 1982) by reverse transcriptase polymerase chain reaction (PCR) employing primers made to the published sequence encoding the amino and carboxyl termini of the receptors (Vigon et al., *Proc. Natl. Acad. Sci. USA* 89: 5640–5644, 1992). Template HEL cell cDNA was synthesized from poly d(T)-selected poly(A)$^+$ RNA using primer ZC5499 (SEQ ID NO: 3). Thirteen µl of HEL cell poly(A)$^+$ RNA at a concentration of 1 µg/µl was mixed with 3 µl of 20 pmole/µl first strand primer ZC5499 (SEQ ID NO: 3). The mixture was heated at 65° C. for 4 minutes and cooled by chilling on ice.

First strand cDNA synthesis was initiated by the addition of 8 µl of first strand buffer (250 mM Tris-HCl, pH 8.3, 375 mM KCl, 15 mM MgCl$_2$) (5× SUPERSCRIPT™ buffer; GIBCO BRL, Gaithersburg, Md.), 4 µl of 100 mM dithiothreitol and 3 µl of a deoxynucleotide triphosphate solution containing 10 mM each of dATP, dGTP, dTTP and 5-methyl-dCTP (Pharmacia LKB Biotechnology Inc., Piscataway, N.J.). The reaction mixture was incubated at 45° C. for 4 minutes followed by the addition of 10 µl of 200 U/µl of RNase H$^-$ reverse transcriptase (SUPERSCRIPT™ reverse transcriptase; GIBCO BRL) to the RNA-primer mixture. The reaction was incubated at 45° C. for 1 hour followed by an incubation at 50 C. for 15 minutes. Sixty µl of TE (10 mM Tris:HCl, pH 8.0, 1 mM EDTA) was added to the reaction followed by chromatography through a 400 pore size gel filtration column (CHROMA SPIN+TE-400™; Clontech Laboratories Inc., Palo Alto, Calif.) to remove excess primer.

First strand HEL cell cDNA was used as a template for the amplification of human MPL-P receptor cDNA using primers corresponding to the region encoding the amino and carboxyl termini of the receptor protein (Vigon et al., ibid.). The primers also each incorporated a different restriction enzyme cleavage site to aid in the directional cloning of the amplified product (ZC5746, SEQ ID NO: 4, containing an Eco RI site; ZC5762, SEQ ID NO: 5, containing an Xho I site). A 100 µl reaction was set up containing 10 ng of template cDNA, 50 pmoles of each primer; 200 µM of each deoxynucleotide triphosphate (Pharmacia LKB Biotechnology Inc.); 1 µl of 10× PCR buffer (Promega Corp., Madison, Wis.); and 10 units of Taq polymerase (Roche Molecular Systems, Inc., Branchburg, N.J.). The polymerase chain reaction was run for 35 cycles (1 minute at 95° C., 1 minute at 60° C. and 2 minutes at 72° C. with 1 extra second added to each successive cycle) followed by a 10 minute incubation at 72° C.

Human MPL-K receptor cDNA was isolated by polymerase chain reaction amplification from HEL cell cDNA in an manner identical to the MPL-P receptor cDNA described above, except primer ZC5762 (SEQ ID NO: 5) was replaced with ZC5742 (SEQ ID NO: 6). PCR primer ZC5742 is specific to the 3' terminus of human MPL-K cDNA and incorporated an Xho I restriction site to facilitate cloning.

The reaction products were extracted twice with phenol/chloroform (1:1), then once with chloroform and were ethanol precipitated. Following digestion with Eco RI and Xho I, the products were fractionated on a 0.8% low melt agarose gel (SEA PLAQUE GTG™ low melt agarose; FMC Corp., Rockland, Me.). A 1.9 Kb amplified product corresponding to human MPL-P receptor cDNA and a 1.7 Kb product corresponding to human MPL-K receptor cDNA were recovered from the excised gel slices by digestion of the gel matrix with β-agarase I (New England Biolabs, Inc., Beverly, Mass.) followed by ethanol precipitation. The cDNAs were subcloned into the vector pBluescript SK+ (Stratagene Cloning Systems, La Jolla, Calif.) for validation by sequencing.

Example II

Isolation of Mouse MPL Receptor cDNA

Spleens from C57BL/KsJ-db/db mice were removed and immediately placed in liquid nitrogen. Total RNA was prepared from spleen tissue using guanidine isothiocyanate (Chirgwin et al., *Biochemistry* 18: 52–94, 1979) followed by a CsCl centrifugation step. Spleen poly(A)+ RNA was isolated using oligo d(T) cellulose chromatography (Aviv and Leder, *Proc. Natl. Acad. Sci. U.S.A.* 69: 1408–1412, 1972).

Seven and a half µl of poly d(T)-selected poly(A)$^+$ mouse spleen RNA at a concentration of 1.7 µg/µl was mixed with 3 µl of 20 pmole/µl first strand primer ZC6091 (SEQ ID NO: 7) containing a Not I restriction site. The mixture was heated at 65° C. for 4 minutes and cooled by chilling on ice. First strand cDNA synthesis was initiated by the addition of 8 µl of 250 mM Tris-HCl, pH 8.3, 375 mM KCl, 15 mM MgCl$_2$ (5× SUPERSCRIPT™ buffer; GIBCO BRL), 4 µl of 100 mM dithiothreitol and 3 µl of a deoxynucleotide triphosphate solution containing 10 mM each of dATP, dGTP, dTTP and 5-methyl-dCTP (Pharmacia LKB Biotechnology Inc.) to the RNA-primer mixture. The reaction mixture was incubated at 45° C. for 4 minutes followed by the addition of 10 µl of 200 U/µl RNase H$^-$ reverse transcriptase (GIBCO BRL). The efficiency of the first strand synthesis was analyzed in a parallel reaction by the addition of 10 µCi of $^{32}$P-αdCTP to a 10 µl aliquot of the reaction mixture to label the reaction for analysis. The reactions were incubated at 45° C. for 1 hour followed by an incubation at 50° C. for 15 minutes. Unincorporated $^{32}$P-αdCTP in the labeled reaction was removed by chromatography on a 400 pore size gel filtration column (CHROMA SPIN+TE-400™; Clontech Laboratories Inc.). Unincorporated nucleotides in the unlabeled first strand reaction were removed by twice precipitating the cDNA in the presence of 8 µg of glycogen carrier, 2.5M ammonium acetate and 2.5 volume ethanol. The unlabeled cDNA was resuspended in 50 µl water for use in second strand synthesis. The length of the labeled first strand cDNA was determined by agarose gel electrophoresis.

Second strand synthesis was performed on first strand cDNA under conditions that promoted first strand priming of second strand synthesis resulting in DNA hairpin formation. The reaction mixture was assembled at room temperature and consisted of 50 µl of the unlabeled first strand cDNA, 16.5 µl water, 20 µl of 5× polymerase I buffer (100 mM Tris:HCl, pH 7.4, 500 mM KCl, 25 mM $MgCl_2$, 50 mM $(NH_4)_2SO_4$), 1 µl of 100 mM dithiothreitol, 2 µl of a solution containing 10 mM of each deoxynucleotide triphosphate, 3 µl of 5 mM β-NAD, 15 µl of 3 U/µl E. coli DNA ligase (New England Biolabs Inc., Beverly, Mass.) and 5 µl of 10 U/µl E. coli DNA polymerase I (Amersham Corp., Arlington Heights, Ill.). The reaction was incubated at room temperature for 5 minutes followed by the addition of 1.5 µl of 2 U/µl RNase H (GIBCO BRL). A parallel reaction in which a 10 µl aliquot of the second strand synthesis mixture was labeled by the addition of 10 µCi $^{32}$P-αdCTP was used to monitor the efficiency of second strand synthesis. The reactions were incubated at 15° C. for two hours followed by a 15 minute incubation at room temperature. Unincorporated $^{32}$P-αdCTP in the labeled reaction was removed by chromatography through a 400 pore size gel filtration column (Clontech Laboratories, Inc.) before analysis by agarose gel electrophoresis. The unlabeled reaction was terminated by two extractions with phenol/chloroform and a chloroform extraction followed by ethanol precipitation in the presence of 2.5M ammonium acetate.

The single-stranded DNA of the hairpin structure was cleaved using mung bean nuclease. The reaction mixture contained 100 µl of second strand cDNA, 20 µl of 10× mung bean nuclease buffer (Stratagene Cloning Systems, La Jolla, Calif.), 16 µl of 100 mM dithiothreitol, 51.5 µl of water and 12.5 µl of a 1:10 dilution of mung bean nuclease (Promega Corp.; final concentration 10.5 U/µl) in mung bean nuclease dilution buffer. The reaction was incubated at 37° C. for 15 minutes. The reaction was terminated by the addition of 20 µl of 1M Tris: HCl, pH 8.0 followed by sequential phenol/chloroform and chloroform extractions as described above. Following the extractions, the DNA was precipitated in ethanol and resuspended in water.

The resuspended cDNA was blunt-ended with T4 DNA polymerase. The cDNA, which was resuspended in 190 µl of water, was mixed with 50 µl 5× T4 DNA polymerase buffer (250 mM Tris:HCl, pH 8.0, 250 mM KCl, 25 mM $MgCl_2$), 3 µl 0.1M dithiothreitol, 3 µl of a solution containing 10 mM of each deoxynucleotide triphosphate and 4 µl of 1 U/µl T4 DNA polymerase (Boehringer Mannheim Corp., Indianapolis, Ind.). After an incubation of 1 hour at 10° C., the reaction was terminated by the addition of 10 µl of 0.5M EDTA followed by serial phenol/chloroform and chloroform extractions as described above. The DNA was chromatographed through a 400 pore size gel filtration column (Clontech Laboratories Inc., Palo Alto, Calif.) to remove trace levels of protein and to remove short cDNAs less than ~400 bp in length. The DNA was ethanol precipitated in the presence of 12 µg glycogen carrier and 2.5M ammonium acetate and was resuspended in 10 µl of water. Based on the incorporation of $^{32}$P-αdCTP, the yield of cDNA was estimated to be ~2 µg from a starting mRNA template of 12.5 µg.

Eco RI adapters were ligated onto the 5' ends of the cDNA to enable cloning into a lambda phage vector. A 10 µl aliquot of cDNA (~2 µg) and 10 µl of 65 pmole/µl of Eco RI adapter (Pharmacia LKB Biotechnology Inc.) were mixed with 2.5 µl 10× ligase buffer (Promega Corp.), 1 µl of 10 mM ATP and 2 µl of 15 U/µl T4 DNA ligase (Promega Corp.). The reaction was incubated overnight (~18 hours) at a temperature gradient of 0° C. to 18° C. The reaction was further incubated overnight at 12° C. The reaction was terminated by the addition of 75 µl of water and 10 µl of 3M Na acetate, followed by incubation at 65° C. for 30 minutes. After incubation, the cDNA was extracted with phenol/chloroform and chloroform as described above and precipitated in the presence of 2.5M ammonium acetate and 1.2 volume of isopropanol. Following centrifugation, the cDNA pellet was washed with 70% ethanol, air dried and resuspended in 89 µl water.

To facilitate the directional cloning of the cDNA into a lambda phage vector, the cDNA was digested with Not I, resulting in a cDNA having 5' Eco RI and 3' Not I cohesive ends. The Not I restriction site at the 3' end of the cDNA had been previously introduced through primer ZG6091 (SEQ ID NO: 7). Restriction enzyme digestion was carried out in a reaction containing 89 µl of cDNA described above, 10 µl of 6 mM Tris:HCl, 6 mM $MgCl_2$, 150 mM NaCl, 1 mM DTT (10× D buffer; Promega Corp., Madison, Wis.) and 1 µl of 12 U/µl Not I (Promega Corp.). Digestion was carried out at 37° C. for 1 hour. The reaction was terminated by serial phenol/chloroform and chloroform extractions. The cDNA was ethanol precipitated, washed with 70% ethanol, air dried and resuspended in 20 µl of 1× gel loading buffer (10 mM Tris:HCl, pH 8.0, 1 mM EDTA, 5% glycerol and 0.125% bromphenol blue).

The resuspended cDNA was heated to 65° C. for 5 minutes, cooled on ice and electrophoresed on a 0.8% low melt agarose gel (SEA PLAQUE GTG™ low melt agarose; FMC Corp.). Unincorporated adapters and cDNA below 1.6 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water (300 µl) approximately three times the volume of the gel slice was added to the tube, and the agarose was melted by heating to 65° C. for 15 minutes. Following equilibration of the sample to 42° C., 10 µl of 1 U/µl β-agarase I (New England Biolabs, Inc.) was added, and the mixture was incubated for 90 minutes to digest the agarose. After incubation, 40 µl of 3M Na acetate was added to the sample, and the mixture was incubated on ice for 15 minutes. The sample was centrifuged at 14,000×g for 15 minutes at room temperature to remove undigested agarose. The cDNA in the supernatant was ethanol precipitated, washed in 70% ethanol, air-dried and resuspended in 37 µl of water for the kinase reaction to phosphorylate the ligated Eco RI adapters.

To the 37 µl cDNA solution described above was added 10 µl 10× ligase buffer (Stratagene Cloning Systems), and the mixture was heated to 65° C. for 5 minutes. The mixture was cooled on ice, and 5 µl 10 mM ATP and 3 µl of 10 U/µl T4 polynucleotide kinase (Stratagene Cloning Systems) were added. The reaction was incubated at 37° C. for 45 minutes and was terminated by heating to 65° C. for 10 minutes followed by serial extractions with phenol/chloroform and chloroform. The phosphorylated cDNA was ethanol precipitated in the presence of 2.5M ammonium acetate, washed with 70% ethanol, air dried and resuspended in 12.5 µl water. The concentration of the phosphorylated cDNA was estimated to be ~40 fmole/µl.

The resulting cDNA was cloned into the lambda phage vector λExcell (Pharmacia LKB Biotechnology Inc.), purchased predigested with Eco RI and Not I and dephosphorylated. Ligation of cDNA to vector was carried out in a reaction containing 2 µl of 20 fmole/µl prepared λExcell phage arms, 4 µl of water, 1 µl 10× ligase buffer (Promega Corp.), 2 µl of 40 fmole/µl cDNA and 1 µl of 15 U/µl T4 DNA ligase (Promega Corp.). Ligation was carried out at 4° C. for 48 hours. Approximately 50% of the ligation mixture was packaged into phage using Gigapack II Gold packaging extract (Stratagene Cloning Systems) according to the directions of the vendor. The resulting cDNA library contained over $1.5 \times 10^7$ independent recombinants with background levels of insertless phage of less than 1.5%.

A $^{32}$P-labeled human MPL-K receptor cDNA probe was used to isolate mouse MPL receptor cDNA from the mouse spleen cDNA phage library. The cDNA library was plated on Sure strain of *E. coli* cells (Stratagene Cloning Systems) at a density of 40,000 to 50,000 PFU/150 mm diameter plate. Phage plaques from thirty-three plates were transferred onto Hybond N™ filters (Amersham Corp., Arlington Heights, Ill.) and processed according to the directions of the manufacturer. The processed filters were baked for 2 hours at 80° C. in a vacuum oven followed by several washes at 70° C. in wash buffer (0.25×SSC, 0.25% SDS, 1 mM EDTA) and prehybridized overnight at 65° C. in hybridization solution (5× SSC, 5× Denhardt's solution, 0.1% SDS, 1 mM EDTA and 100 µg/ml heat denatured salmon sperm DNA) in a hybridization oven (model HB-2; Techne Inc., Princeton, N.J.). Following prehybridization, the hybridization solution was discarded and replaced with fresh hybridization solution containing approximately $2 \times 10^6$ cpm/ml of $^{32}$P-labeled human MPL-K cDNA prepared by the use of a commercially available labeling kit (MEGAPRIME™ kit; Amersham Corp., Arlington Heights, Ill.). The probe was denatured at 98° C. for 5 minutes before being added to the hybridization solution. Hybridization was at 65° C. overnight. The filters were washed at 55° C. in wash buffer (0.25×SSC, 0.25% SDS, 1 mM EDTA) and were autoradiographed with intensifying screens for 4 days at −70° C. on XAR-5 film (Kodak Inc., Rockchester, N.Y.). Employing the autoradiograph as template, agar plugs were recovered from regions of the plates corresponding to primary signals and were soaked in SM (0.1M NaCl; 50 mM Tris:HCl, pH 7.5, 0.02% gelatin) to elute phage for plaque purification. Seven plaque-purified phages were isolated that carried inserts hybridizing to the human MPL-K receptor probe. The phagemids contained within the λ Excell phage were recovered using the in vivo recombination system in accordance with the directions of the vendor. The identity of the cDNA inserts was confirmed by DNA sequencing.

The isolated clones encoded a protein exhibiting a high degree of sequence indentity to human MPL-P receptor and to a recently reported mouse MPL receptor (Skoda et al., *EMBO J.* 12: 2645-2653, 1993). The seven clones fell into two classes differing from each other by three clones having a deletion of sequences encoding a stretch of 60 amino acid residues near the N-terminus. The cDNA encoding the protein without the deletion was referred to as mouse Type I MPL receptor cDNA. Type II receptor cDNA lacked sequences encoding Type I receptor residues 131 to 190 of SEQ ID NO: 17. In addition, Type I and II receptors differed from the reported mouse MPL receptor sequence (Skoda et al., ibid.) by the presence of a sequence encoding the amino acid residues Val-Arg-Thr-Ser-Pro-Ala-Gly-Glu (SEQ ID NO: 9) inserted after amino acid residue 222 and by a substitution of a glycine residue for serine at position 241 (positions refer to the Type I mouse receptor).

Type I and II mouse MPL receptor cDNAs were subcloned into vector pHZ-1 for expression in mammalian cells. Plasmid pHZ-1 is an expression vector that may be used to express protein in mammalian cells or in a frog oocyte translation system from mRNAs that have been transcribed in vitro. The pHZ-1 expression unit comprises the mouse metallothionein-1 promoter, the bacteriophage T7 promoter flanked by multiple cloning banks containing unique restriction sites for insertion of coding sequences, the human growth hormone terminator and the bacteriophage T7 terminator. In addition, pHZ-1 contains an *E. coli* origin of replication; a bacterial beta lactamase gene; a mammalian selectable marker expression unit comprising the SV40 promoter and origin, a neomycin resistance gene and the SV40 transcription terminator. To facilate directional cloning into pHZ-1, a polymerase chain reaction employing appropriate primers was used to create an Eco RI site and a Xho I site upstream from the translation initation codon and downstream from the translation termination codon, respectively. The polymerase chain reaction was carried out in a mixture containing 10 µl 10× ULTMA™ DNA polymerase buffer (Roche Molecular Systems, Inc., Branchburg, N.J.), 6 µl of 25 mM MgCl$_2$, 0.2 µl of a deoxynucleotide triphosphate solution containing 10 mM each of dATP, dGTP, dTTP and dCTP (Pharmacia LKB Biotechnology Inc.), 2.5 µl of 20 pmole/µl primer ZC6603 (SEQ ID NO: 8), 2.5 µl of 20 pmole/µl primer ZC5762 (SEQ ID NO: 5), 32.8 µl of water, 1 µl of an early log phase bacterial culture harboring either a Type I or a Type II mouse MPL receptor plasmid and 1 µl of 6 U/µl DNA polymerase (ULTMA™ polymerase; Roche Molecular Systems, Inc., Branchburg, N.J.). AmpliWax™ (Roche Molecular Systems, Inc.) was employed in the reaction according to the directions of the vendor. The polymerase chain reaction was run for 25 cycles (1 minute at 95° C., 1 minute at 55° C. and 3 minutes at 72° C.) followed by a 10 minute incubation at 72° c. The amplified products were serially extracted with phenol/chloroform and chloroform, then ethanol precipitated in the presence of 6 µg glycogen carrier and 2.5M ammonium acetate. The pellets were resuspended in 87 µl of water to which was added 10 µl of 10×H buffer (Boehringer Mannheim Corp.), 2 µl of 10 U/µl Eco RI (Boehringer Mannheim) and 1 µl of 40 U/µl Xho I (Boehringer Mannheim Corp.). Digestion was carried out at 37° C. for 1 hour. The reaction was terminated by heating to 65° C. for 15 minutes and chromatographed through a 400 pore size gel filtration column (CHROMA SPIN+TE-400™; Clontech Laboratories Inc.).

The isolated receptor inserts described above were ligated into Eco RI and Xho I digested and dephosphorylated pHZ-1 vector. The ligation reaction contained 1 µl of 50 ng/µl prepared pHZ-1 vector, 5 µl of 5 ng/µl cDNA insert, 2 µl of 10× ligase buffer (Promega Corp.), 11.75 µl water and 0.25 µl of 4 U/µl T4 DNA ligase (Stratagene Cloning Systems). Ligation was carried out at 10° C. overnight. The ligated DNAs were transfected into *E. coli* (MAX EFFICIENCY DH10B™ competent cells; GIBCO BRL) in accordance with the vendor's directions. The validity of Type I and Type II mouse MPL and human MPL-P receptor inserts in pHZ-1 was confirmed by DNA sequencing. The resulting plasmids pSLmpl-8 and pSLmpl-9 carried the mouse Type II and Type I MPL receptor cDNAs, respectively. Plasmid pSLmpl-44 carried the human MPL-P cDNA insert.

Example III

Construction of BaF3 Cell Lines Expressing MPL Receptors

BaF3, an interleukin-3 dependent pre-lymphoid cell line derived from murine bone marrow (Palacios and Steinmetz, *Cell* 41: 727–734, 1985; Mathey-Prevot et al., *Mol. Cell. Biol.* 6: 4133–4135, 1986), was maintained in complete media (RPMI 1640 medium (JRH Bioscience Inc., Lenexa, Kans.) supplemented with 10% heat-inactivated fetal calf serum, 4% conditioned media from cultured WEHI-3 cells (Becton Dickinson Labware, Bedford, Mass.), 2 mM L-glutamine, 2-mercaptoethanol (1:280,000 final conc.) and PSN antibiotics (GIBCO BRL)). Cesium chloride purified plasmids pSLmpl-8, pSLmpl-9 and pSLmpl-44 were linearized at the Nde I site prior to electroporation into BaF3 cells. BaF3 cells for electroporation were washed once in RPMI 1640 media and resuspended in RPMI 1640 media at a cell density of $10^7$ cells/ml. One ml of resuspended BaF3 cells was mixed with 30 µg of each of the linearized plasmid DNAs and transferred to separate disposable electroporation chambers (GIBCO BRL). Following a 15 minute incubation at room temperature the cells were given two serial shocks (800 µFad/300 V.; 1180 µFad/300 V.) delivered by an electroporation apparatus (CELL-PORATOR™; GIBCO BRL). After a 5 minute recovery time, the electroporated cells were transferred to 10 ml of complete media and placed in an incubator for 15–24 hours (37° C., 5% $CO_2$). The cells were then spun down and resuspended in 10 ml of complete media containing 1600 µg/ml G418 and plated at limiting dilutions in 96-well tissue culture plates to isolate G418-resistant clones. Expression of MPL receptors in G418-resistant BaF3 clones was inferred by Northern blot analysis of BaF3 mRNA for the presence of MPL receptor transcript. A cell line designated BaF3/MPLR1.1 was found to express high levels of Type I mouse MPL receptor mRNA and was used for subsequent assay for MPL ligand activity in conditioned media of transfected BHK 570 cells. A BaF3 cell line expressing Type II receptor mRNA was designated as BaF3/MPLR2.

Example IV

Production of Soluble Mouse MPL Receptor

A mammalian expression plasmid encoding soluble mouse Type I MPL receptor (pLDmpl-53) was produced by combining DNA segments from pSLmpl-9, a mammalian expression plasmid containing the cDNA encoding full-length mouse Type I MPL receptor described above, with a DNA segment from pSLmpl-26, an expression plasmid constructed to produce the soluble mouse Type I MPL receptor in bacteria.

A cDNA segment encoding mouse Type I MPL soluble receptor was isolated by PCR employing primers ZC6704 (SEQ ID NO: 10) and ZC6703 (SEQ ID NO: 11) using full-length receptor plasmid pSLmpl-9 as template. To facilitate directional cloning, primers ZC6704 and ZC6703 incorporated Eco RI and Xho I restriction sites at their respective 5' ends. Primer ZC6703 also encoded an inframe consensus target sequence for protein kinase to enable in vitro labeling of the purified soluble receptor with $^{32}P$ γ-ATP (Li et al., *Proc. Natl. Acad. Sci. U.S.A.* 86: 558–562, 1989). The PCR was carried out in a mixture containing 10 µl 10× ULTMA™ DNA polymerase buffer (Roche Molecular Systems, Inc.), 6 µl of 25 mM $MgCl_2$, 0.2 µl of a deoxynucleotide triphosphate solution containing 10 mM each of dATP, dGTP, dTTP and dCTP (Pharmacia LKB Biotechnology Inc.), 11 µl of 4.55 pmole/µl primer ZC6704 (SEQ ID NO: 10), 21 µl of 2.43 pmole/µl primer ZC6703 (SEQ ID NO: 11), 50.3 µl of water, 1 µl 50 ng/µl Hind III and Xba I digested pSLmpl-9 and 1 µl of 6 U/µl ULTMA™ DNA polymerase (Roche Molecular Systems, Inc.). AmpliWax™ (Roche Molecular Systems, Inc.) was employed in the reaction according to the directions of the vendor. The polymerase chain reaction was run for 3 cycles (1 minute at 95° C., 1 minute at 50° C. and 2 minutes at 72° C.) followed by 11 cycles at increased hybridization stringency (1 minute at 95° C., 30 seconds at 55° C. and 2 minutes at 72° C.) followed by a 10 minute incubation at 72° C. The amplified product was serially extracted with phenol/chloroform and chloroform followed by chromatography through a 400 pore size gel filtration column (Clontech Laboratories, Inc.). The PCR product was ethanol precipitated in the presence of 20 µg glycogen carrier and 2.5M ammonium acetate. The pellet was resuspended in 32 µl of water. To 16 µl of the resuspended PCR product was added 2 µl 10× H buffer (Boehringer Mannheim Corp.), 1 µl of 10 U/µl Eco RI (Boehringer Mannheim Corp.) and 1 µl of 40 U/µl Xho I (Boehringer Mannheim Corp.). Digestion was carried out at 37° C. for 1 hour. Digestion was terminated by heating to 65° C. for 15 minutes and was purified on a 0.7% low-melt agarose gel. Fragment recovery from low-melt agarose was done by digestion of the gel matrix with β-agarase I (New England Biolabs).

The resulting PCR product encoded the N-terminal extracellular domain of mouse Type I MPL receptor (residues 27 to 480 of SEQ ID NO: 17). In the absence of the putative receptor trans-membrane domain (residues 483 to 504 of SEQ ID NO: 17) the expressed protein is expected to be secreted in the presence of a suitable signal peptide. A mouse Type II soluble MPL receptor encoding cDNA was obtained using the PCR conditions described above except that pSLmpl-8 was used as template. The validity of both receptor fragments was confirmed by DNA sequencing.

The soluble mouse Type I and Type II MPL receptor encoding DNA fragments were cloned into Eco RI and Xho I digested vector pOmpA2-5 to yield pSLmpl-26 and pSLmpl-27, respectively. Plasmid pOmpA2-5 is a modification of pOmpA2 (Ghrayab et al., *EMBO J.* 3: 2437–2442, 1984), a bacterial expression vector designed to target the recombinant protein to the periplasmic space. pOmpA2-5 was constructed by replacement of a 13 bp sequence between the Eco RI and Bam HI sites of pOmpA2 with a synthetic 42 bp sequence. The sequence was created by annealing of two 42 nt complementary oligonucleotides (ZC6707, SEQ ID NO: 12; ZC 6706, SEQ ID NO: 13), which when base paired formed Eco RI and Bam HI cohesive ends, facilitating directional cloning into Eco RI and Bam HI digested pOmpA2. Within the inserted sequence is an Xho I site inframed with respect to a bacterial leader sequence and to the mouse MPL soluble receptor encoding cDNAs described above, as well as an inframe tract of 6 histidine codons located 3' of the Xho I site to enable the recombinant protein to be purified by metal chelation affinity chromatography (Houchuli et al., *Bio/Technol.* 6: 1321–1325, 1988). Following the sequence encoding the histidine tract was an inframe termination codon. The validity of the pOmpA2-5, pSLmpl-26 and pSLmpl-27 was confirmed by DNA sequencing.

pLDmpl-53, a mammalian expression plasmid producing soluble mouse Type I MPL receptor, was constructed by combining DNA segments from pSLmpl-9 and pSLmpl-26 into expression vector pHZ-200 (pHZ-1 in which a dihydrofolate reductase sequence was substituted for the neomycin resistance gene). The 1164 bp Eco RI/Bam HI cDNA fragment from pSLmpl-9 replaced the mammalian signal sequence deleted during the construction of bacterial expression plasmid pSLmpl-26. The 416 bp Bam HI fragment from pSLmpl-26 supplied the coding sequence for the carboxy-terminal portion of the soluble MPL receptor, the kinase labeling domain, the poly-histidine tract and the translation terminator. The two fragments were gel purified and cloned into the Eco RI/Bam HI sites of pBluescript KS+ (Stratagene Cloning Systems) to yield plasmid pBS8.76LD-5. Correct orientation of the the 416 bp pSLmpl-26 derived Bam HI fragment with respect to the 1164 bp pSLmpl-9 derived Eco RI/Bam HI fragment in pBS8.76LD-5 was determined by PCR using primers ZC 6603 (SEQ ID NO: 8) and ZC 6703 (SEQ ID NO: 11). The Xba I site within the poly-linker sequence of pBS8.76LD-5 enabled the reconstituted receptor cDNA to be excised as an 1.5 kb Eco RI/Xba I fragment for cloning into pHZ-200 following digestion of the vector with Eco RI and Xba I. The resulting mammalian expression plasmid, pLDmpl-53, was prepared in large scale for transfection into BHK cells.

Twenty micrograms of purified pLDmpl-53 plasmid was transfected into BHK 570 cells using the calcium phosphate precipitation method. After 5 hours, the cells were shocked with 15% glycerol for 3 minutes to facilitate uptake of DNA. Fresh growth media was added overnight. The following day the cells were split at various dilutions, and selection media containing 1 µM methotrexate was added. After approximately two weeks, discrete, methotrexate-resistant colonies were visible. Resistant colonies were either pooled or maintained as distinct clones. Spent media from the pooled colonies was immediately tested for presence of soluble MPL receptor protein.

Soluble MPL receptor protein was isolated through the interaction of the poly-histidine tract present on the carboxy-terminal of the protein with a metal chelation resin containing immobilized $Ni^{2+}$ (HIS-BIND™; Novagen, Madison, Wis.). Serum-free spent culture media from the pLDmpl-53 pool was passed over the resin, and bound protein was eluted with imidazole. SDS-PAGE analysis revealed a single band at ~67 kDa. This protein was subjected to N-terminal amino acid analysis and confirmed to be mouse MPL receptor.

Soluble mouse MPL receptor was purified from a pool of BHK transfectants, which had been transfected with soluble mouse Type I MPL receptor expressing plasmid, pLDmpl-53. The purified soluble receptor was immobilized on CNBr-activated SEPHAROSE™ 4B (Pharmacia LKB Biotechnology, Inc.) matrix essentially as directed by the manufacturer and used for affinity purification of the MPL activity in conditioned media of 24-11-5 cells. The affinity matrix was packed in a XK16 column (Pharmacia LKB Biotechnology Inc.). Conditioned media from 24-11-5 cells were concentrated on a 10 Kd cut off Hollow Fiber Membrane (A/G Technology Corp., Needham, Mass.) and loaded onto the bottom of the MPL receptor affinity column at a flow rate of 1 ml/minute. The column was washed with phosphate buffed saline (PBS) containing 0.5M NaCl and 0.01% sodium azide. MPL activity was eluted from the column with 3M potassium thiocyanate (Sigma Chemical Company, St. Louis, Mo.) at a flow rate of 0.5 ml/minute. Potassium thiocyanate was removed by dialysis against PBS. Active fractions were identified by MTT proliferation assay.

Example V

Isolation and Characterization of a MPL Receptor Ligand Expressing Cell Line

BaF3/MPLR1.1 cells are IL-3 dependent cells expressing a stabley transfected Type I mouse MPL receptor. A mutagenesis and selection scheme was devised to isolate cell lines expressing the MPL receptor ligand by mutagenizing BaF3/MPLR1.1 cells, and selecting for autocrine growth in the absence of exogenous IL-3.

Approximately $1.2 \times 10^6$ BaF3/MPLR1.1 cells were pelleted and washed with GM (RPMI 1640 media supplemented with 2-mercaptoethanol (1:240,000 final concentration), 2 mM L-glutamine, 110 µg/ml sodium pyruvate, 50 µg/ml G418 and 10% heat inactivated fetal bovine serum). The cells were resuspended in 2 ml of GM containing 0.15% (v/v) of the mutagen 2-ethylmethanesulfonate (EMS) and incubated for 2 hours at 37° C. After incubation, the cells were washed once in PBS and once in GM and plated onto 10 cm plates at density of approximately 40,000 cells/ml in GM supplemented with 5% WEHI-3 conditioned media (Becton Dickinson Labware, Bedford, Mass.) as a source of IL-3. The cells were allowed a recovery period of seven days incubated at 37° C. under 5% $CO_2$ before selection for IL-3 independent growth. Following the recovery period, the culture was dense with viable cells. The cells were washed with GM and were cultured in GM in the absence of WEHI-3 conditioned media. After eleven days of selection, small numbers of viable cells were observed. The viable cell density of the IL-3 independent culture was estimated to be 250 cells/ml. One ml of the IL-3 independent culture was plated onto each of 19 wells of a 24-well culture plate for further characterization.

Conditioned media from the above IL-3 growth independent BaF3/MPLR1.1 cells were assayed for proliferative activity on BaF3/MPLR cells. Conditioned media from all nineteen IL-3 growth independent pools were found to have activity in the MTT proliferatation assay (disclosed in Example VII). The positive media were reassayed for proliferative activity in the presence of 2 µg/ml rat anti-mouse IL-3, or anti-mouse IL-4 or in the presence of both neutralizing antibodies (Pharmingen, San Diego, Calif.) to identify IL-3 growth independent mutants expressing those cytokines. (In a previous experiment, it was found that BaF3 cells also responded to IL-4.) Only conditioned medium from cells from plate #11 (designated "24-11" cells) was found to have activity that was not neutralized by IL-3 or IL-4 antibodies.

The mutagenesis and selection scheme described above was applied to five other BaF3/MPLR1 clones (BaF3/MPLR1 clones #4, 9, 12, 15 and 18, designated as BaF3/MPLR1.4, 0.9, 0.12, 0.15 and 0.18, respectively). Seventeen isolates were found to have conditioned media which stimulated proliferation of BaF3/MPLR1 cells. Activity of all the media was found to be neutralized by anti-IL-3 or IL-4 antibodies alone or in combination. These clones were not characterized further.

The proliferative activity of conditioned media from the 24-11 pool was characterized in detail. The 24-11 pool was subdivided into nineteen subpools and conditioned media were retested for activity. All nineteen subpools (i.e. 24-11-1 thru 24-11-19) stimulated proliferation of IL-3 growth dependent BaF3/MPLR1 cells in the absence of exogenous IL-3. The activity was not inhibited by IL-3 or IL-4 neutralizing antibodies or by a combination of both antibodies.

Two experiments were performed to determine the specificity of the 24-11 activity. The conditioned media were assayed for proliferative activity on control BaF3 cells that do not express the MPL receptor. In the absence of exogenous IL-3, proliferation of control BaF3 cells was not observed in the conditioned media from any of the nineteen 24-11 subpools. In a second experiment, proliferation activity was assayed for inhibition by purified soluble MPL receptor. BaF3/MPLR1 cells were cultured in GM media supplemented with 50% 24-11 conditioned media. To each sample was added Type I mouse soluble MPL receptor to a final concentration of 0.0, 0.625, 1.25, 2.5 or 5.0 µg/ml. The result was scored 4 days later by MTT cell proliferation assay. The proliferative activity of the 24-11 conditioned media was completely blocked at 0.625 to 1.25 µg/ml soluble MPL receptor. Soluble receptor concentrations that completely inhibited activity had no effect on IL-3 or IL-4 stimulation of BaF3/MPLR1 cells. The results indicated that soluble MPL receptor competed for the stimulatory activity of 24-11 media and is consistent with the hypothesis that 24-11 cells expressed the MPL receptor ligand.

Clones derived from 24-11 cells were isolated by plating at limiting dilutions. One clone, designated 24-11-5 #3, showed a high level of proliferative activity in its conditioned media relative to the 24-11 pool. The proliferative activity was found to be equal to a 1:2000 dilution of conditioned media from WEHI-3 cells (Becton Dickinson Labware).

Example VI

Construction of 24-11-5#3 cDNA library

Total RNA was prepared from ~2.7×10$^8$ 24-11-5#3 cells using guanidine isothiocyanate followed by CsCl centrifugation (Chirgwin et al., ibid.). Poly(A)$^+$ RNA was isolated using an OLIGOTEX-dT-mRNA isolation kit (Qiagen Inc., Chatsworth, Calif.) following the manufacturer's instructions.

First strand cDNA from 24-11-5#3 cells was synthesized in 4 separate parallel reactions. Each reaction contained 7 µl of poly d(T)-selected poly(A)$^+$ 24-11-5#3 RNA at a concentration of 1.6 µg/µl and 2.5 µl of 20 pmole/µl first strand primer ZC6172 (SEQ ID NO: 14) containing an Xho I restriction site. The mixture was heated at 65° C. for 4 minutes and cooled by chilling on ice. First strand cDNA synthesis was initiated by the addition of 8 µl of first strand buffer (5× SUPERSCRIPT™ buffer; GIBCO BRL), 4 µl of 100 mM dithiothreitol and 2 µl of a deoxynucleotide triphosphate solution containing 10 mM each of dATP, dGTP, dTTP and 5-methyl-dCTP (Pharmacia LKB Biotechnology Inc.) to the RNA-primer mixture. The reaction mixture was incubated at 45° C. for 4 minutes followed by the addition of 10 µl of 200 U/µl RNase H$^-$ reverse transcriptase (GIBCO BRL). The efficiency of the first strand synthesis was analyzed in a parallel reaction by the addition of 10 µCi of $^{32}$P-αdCTP to a 10 µl aliquot from one of the reaction mixtures to label the reaction for analysis. The reactions were incubated at 45° C. for 1 hour followed by an incubation at 50° C. for 15 minutes. Unincorporated $^{32}$P-αdCTP in the labeled reaction was removed by chromatography on a 400 pore size gel filtration column (Clontech Laboratories). The unlabeled first strand reactions were pooled, and unincorporated nucleotides were removed by twice precipitating the cDNA in the presence of 32 µg of glycogen carrier, 2.5M ammonium acetate and 2.5 volume ethanol. The unlabeled cDNA was resuspended in 144 µl water for use in second strand synthesis. The length of labeled first strand cDNA was determined by agarose gel electrophoresis.

Second strand synthesis was performed on the first strand cDNA under conditions that promoted first strand priming of second strand synthesis resulting in DNA hairpin formation. Three separate parallel second strand reactions were performed. Each second strand reaction contained 48 µl of the unlabeled first strand cDNA, 16.5 µl of water, 20 µl of 5× polymerase I buffer (100 mM Tris: HCl, pH 7.4, 500 mM KCl, 25 mM MgCl$_2$, 50 mM (NH$_4$)$_2$SO$_4$), 1 µl of 100 mM dithiothreitol, 1 µl of a solution containing 10 mM of each deoxynucleotide triphosphate, 3 µl of 5 mM β-NAD, 1 µl of 3 U/µl E. coli DNA ligase (New England Biolabs Inc.) and 5 µl of 10 U/µl E. coli DNA polymerase I (Amersham Corp.). The reaction was assembled at room temperature and was incubated at room temperature for 5 minutes followed by the addition of 1.5 µl of 2 U/µl RNase H (GIBCO BRL). A 10 µl aliquot from one of the second strand synthesis reactions was labeled by the addition of 10 µCi $^{32}$P-αdCTP to monitor the efficiency of second strand synthesis. The reactions were incubated at 15° C. for two hours followed by a 15 minute incubation at room temperature. Unincorporated $^{32}$P-αdCTP in the labeled reaction was removed by chromatography through a 400 pore size gel filtration column (Clontech Laboratories) before analysis by agarose gel electrophoresis. The unlabeled reactions were pooled and extracted with phenol/chloroform and chloroform followed by ethanol precipitation in the presence of 2.5M ammonium acetate.

The single-stranded DNA of the hairpin structure was cleaved using mung bean nuclease. The reaction mixture contained 100 µl of second strand cDNA, 20 µl of 10× mung bean nuclease buffer (Stratagene Cloning Systems), 16 µl of 100 mM dithiothreitol, 48 µl of water, 10 µl of mung bean nuclease dilution buffer (Stratagene Cloning Systems) and 6 µl of 50 U/µl mung bean nuclease (Promega Corp.). The reaction was incubated at 37° C. for 30 minutes. The reaction was terminated by the addition of 20 µl of 1M Tris: HCl, pH 8.0 followed by sequential phenol/chloroform and chloroform extractions as described above. Following the extractions, the DNA was precipitated in ethanol and resuspended in water.

The resuspended cDNA was blunt-ended with T4 DNA polymerase. The cDNA, which was resuspended in 188 µl of water, was mixed with 50 µl 5× T4 DNA polymerase buffer (250 mM Tris:HCl, pH 8.0, 250 mM KCl, 25 mM MgCl$_2$), 3 µl 0.1M dithiothreitol, 4 µl of a solution containing 10 mM of each deoxynucleotide triphosphate and 5 µl of 1 U/µl T4 DNA polymerase (Boehringer Mannheim Corp.). After an incubation of 30 minutes at 15° C., the reaction was terminated by the addition of 10 µl of 0.5M EDTA followed by serial phenol/chloroform and chloroform extractions as described above. The DNA was chromatographed through a 400 pore size gel filtration column (Clontech Laboratories Inc.) to remove trace levels of protein and to remove short cDNAs less than ~400 bp in length. The DNA was ethanol precipitated in the presence of 10 µg glycogen carrier and 2.5M ammonium acetate and was resuspended 15 µl of water. Based on the incorporation of $^{32}$P-αdCTP, the yield of cDNA was estimated to be ~8 µg from a starting mRNA template of 40 µg.

Eco RI adapters were ligated onto the 5' ends of the cDNA described above to enable cloning into an expression vector. A 10 µl aliquot of cDNA (~5 µg) and 21 µl of 65 pmole/µl of Eco RI adapter (Pharmacia LKB Biotechnology Inc.) were mixed with 4 µl 10× ligase buffer (Promega Corp.), 3 µl of 10 mM ATP and 3 µl of 15 U/µl T4 DNA ligase (Promega Corp.). The reaction was incubated overnight (~48 hours) at 9° C. The reaction was terminated by the addition of 140 μl of water, 20 μl of 10× H buffer (Boehringer Mannheim Corp.) and incubation at 65° C. for 40 minutes. After incubation, the cDNA was extracted with phenol/chloroform and chloroform as described above and precipitated in the presence of 2.5M ammonium acetate and 1.2 volume of isopropanol. Following centrifugation, the cDNA pellet was washed with 70% ethanol, air dried and resuspended in 89 μl water.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced using the ZC6172 primer (SEQ ID NO: 14). Restriction enzyme digestion was carried out in a reaction mixture containing 89 μl of cDNA described above, 10 μl of 10× H buffer (Promega Corp.) and 1.5 μl of 40 U/μl Xho I (Boehringer Mannheim Corp.). Digestion was carried out at 37° C. for 1 hour. The reaction was terminated by serial phenol/chloroform and chloroform extractions and chromatography through a 400 pore size gel filtration column (Clontech Laboratories Inc.).

The cDNA was ethanol precipitated, washed with 70% ethanol, air dried and resuspended in 20 μl of 1× gel loading buffer (10 mM Tris:HCl, pH 8.0, 1 mM EDTA, 5% glycerol and 0.125% bromphenol blue). The resuspended cDNA was heated to 65° C. for 5 minutes, cooled on ice and electrophoresed on a 0.8% low melt agarose gel (SEA PLAQUE GTG™ low melt agarose; FMC Corp.). The contaminating adapters and cDNA below 0.5 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 μl) was added to the tube, and the agarose was melted by heating to 65° C. for 15 minutes. Following equilibration of the sample to 45° C., 5 μl of 1 U/μl β-agarase I (New England Biolabs, Inc.) was added, and the mixture was incubated for 90 minutes at 45° C. to digest the agarose. After incubation, 40 μl of 3M Na acetate was added to the sample, and the mixture was incubated on ice for 15 minutes. The sample was centrifuged at 14,000×g for 15 minutes at room temperature to remove undigested agarose followed by chromatography through a 400 pore size gel filtration column (Clontech Laboratories). The cDNA was ethanol precipitated, washed in 70% ethanol, air-dried and resuspended in 70 μl water for the kinase reaction to phosphorylate the ligated Eco RI adapters.

To the 70 μl cDNA solution was added 10 μl 10× ligase buffer (Stratagene Cloning Systems), and the mixture was heated to 65° C. for 5 minutes. The mixture was cooled on ice, and 16 μl 10 mM ATP and 4 μl of 10 U/μl T4 polynucleotide kinase (Stratagene Cloning Systems) were added. The reaction mixture was incubated at 37° C. for 1 hour and was terminated by heating to 65° C. for 10 minutes followed by serial extractions with phenol/chloroform and chloroform. The phosphorylated cDNA was ethanol precipitated in the presence of 2.5M ammonium acetate, washed with 70% ethanol, air dried and resuspended in 10 μl of water. The concentration of the phosphorylated cDNA was estimated to be ~40 fmole/μl.

Figure 2:
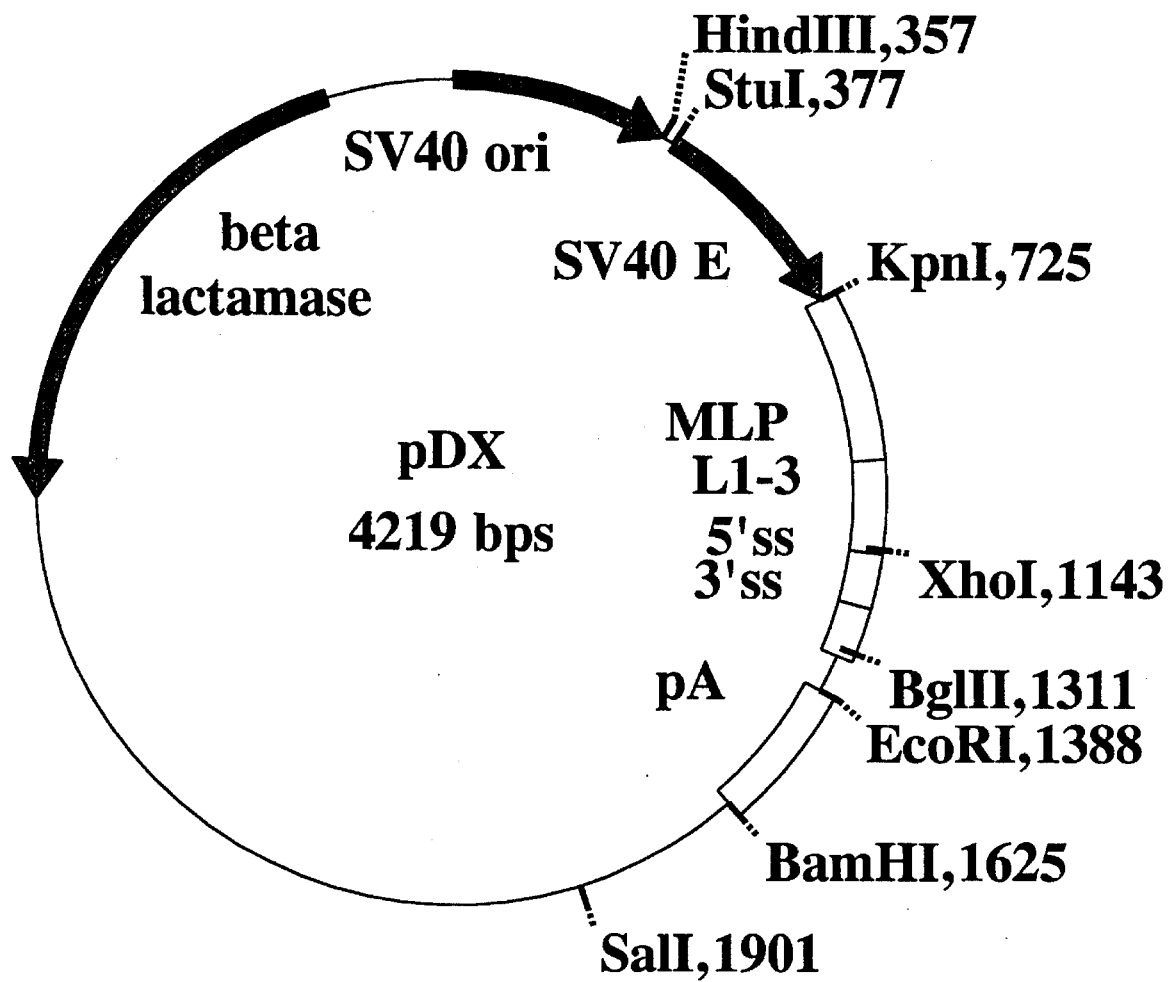
FIG. 2 is a partial restriction map of the vector pDX. Symbols used ase SV40 ori, the origin of replication from SV40; SV40 E, the SV40 enhancer; MLP, adenovirus major late promoter; L1-3, adenovirus tripartite leader; ss, splicing signals; pA, polyadenylation site.

The pDX mammalian expression vector (disclosed in U.S. Pat. No. 4,959,318) (FIG. 2) was modified to accept 24-11-5#3 cDNA that had been synthesized with Eco RI-Xho I ends. An endogeneous Sal I site on pDX was eliminated by digesting the plasmid with Sal I and recircularizing the plasmid following blunting of the Sal I cohesive ends with T4 DNA polymerase. The recircularized plasmid was digested with Eco RI and to it was ligated a short polylinker sequence consisting of two complementary oligonucleotides, ZC6936 (SEQ ID NO: 15) and ZC6937 (SEQ ID NO: 16), to yield plasmid pDX.ES. The introduced polylinker sequence on pDX.ES contained Eco RI and Sal I sites to facilitate directional cloning of 24-11-5 cDNA synthesized with Eco RI-Xho I ends.

A plasmid cDNA library was prepared by ligating Eco RI-Xho I 24-11-5 cDNA into Eco RI/Sal I digested pDX.ES. The ligation mixture was electroporated into *E. coli* (ELECTROMAX DH10B™ competent cells; GIBCO BRL, Gaithersburg, Md.) using a gene pulser/pulse controller and 0.2 cm cuvette (Bio-Rad Laboratories, Hercules, Calif.) employing a 0.2 KV, 400 ohm and 25 μFAD. The cells were diluted to 1.5 ml in Luria broth and incubated at 37° C. for 45 minutes followed by the addition of 0.75 ml of 50% glycerol. The transfected cells were aliquotted and stored at −70° C. until use. Eighty fmoles of cDNA gave rise to over 700,000 independent recombinant plasmids.

Example VII

Expression Screening of 24-11-5 cDNA Library for MPL Activity

The 24-11-5#3 cDNA library was plated onto approximately two thousand 10 cm diameter Luria broth agar plates supplemented with 100 μg/ml ampicillin. The plating density was between 200 to 250 bacterial colonies per plate. Plasmid DNA for transfection into BHK 570 cells was prepared from each bacterial plate using Magic minipreps DNA purification resin (Promega Corp.), according to the manufacturer's instruction. Plasmid DNAs were stored at −20° C. until transfection into BHK 570 cells.

Plasmid pools of 24-11-5#3 cDNA, each containing approximately 200 to 250 cDNA clones were transfected into BHK 570 cells using LIPOFECTAMINE™ (GIBCO BRL). Twenty μl of 30 ng/μl DNA was added to 20 μl of a 1:10 dilution of LIPOFECTAMINE™ solution and incubated at room temperature for 30 minutes. Following the incubation, 160 μl of serum-free media (Hams F12: Dulbeccos MEM (1:1) suplemented with 2 mM L-glutamine, 0.11 mg/ml sodium pyruvate, 5 μg/ml insulin, 5 μg/ml fetuin, 10 μg/ml transferrin, 2 ng/ml selenium IV oxide and 25 mM HEPES buffer) were added to the DNA/LIPOFECTAMINE™ mixture and transferred to a 24 well microtiter plate containing ~100,000 BHK 570 cells. The cells were incubated at 37° C. under 5% $CO_2$ for 4 hours, after which was added 200 ml of BHK Growth Media (Dulbecco's modified Eagles's media suplemented with 2 mM L-glutamine, 0.11 mg/ml sodium pyruvate, 5% heat inactivated fetal calf serum and 100× PSN antibiotics (GIBCO BRL)). The cells were incubated for 16 hours. The media was removed and replaced with 0.5 ml of fresh BHK Growth Media, which was conditioned for 48 hours before being assayed for MPL activity.

A cell proliferation assay was used to detect the presence of MPL activity in conditioned media of library transfected BHK 570 cells. One hundred μl of conditioned media was added to 100 μl of $10^5$/ml washed BaF3/MPLR1.1 cells in RPMI 1640 media (JRH Bioscience Inc., Lenexa, Kans.) supplemented with 2 mM L-glutamine, PSN antibiotics (GIBCO BRL), 0.00036% 2 mercaptoethanol and 10% heat inactivated fetal calf serum. The assay cells were incubated for 3 days at 37° C. under 5% $CO_2$ before assaying for proliferation.

Cell proliferation in the presence of MPL was quantified using a colorimetric assay based on the metabolic breakdown of 3-(4,5-dimethylthiazol-2-yl)-2,5-diphenyl tetrazolium bromide (MTT) (Mosman, *J. Immunol. Meth.* 65: 55–63, 1983). Twenty μl of a 10 mg/ml solution of MTT (Polyscience, Inc., Warrington, Pa.) was added to 100 μl of BaF3/MPLR1.1 assay cells, and the cells were incubated at 37° c. After 4 hours, 200 μl of 0.04N HCl in isopropanol was added, the solution was mixed, and the adsorbance of the sample was read at 570 nm on a model EL320 ELISA reader (Bio-Tek Instruments Inc., Highland Park, Vt.).

One plasmid pool found to be positive, designated T1081, was transfected into BHK 570 cells. Supernatant from the transfectants gave a positive signal in the MTT proliferation assay. PCR and antibody neutralization experiments demonstrated that the activity was not due to IL-3 or IL-4.

Plasmids from the positive pool were used to transform *E. coli* DH10B, and cells were plated (42 plates with approximately 15–20 colonies per plate, 10 plates with approximately 90 colonies per plate and 8 plates with approximately 250 colonies per plate). A replica of each plate was made and stored at 4° C. The colonies on the original plates were scraped and allowed to outgrow in liquid culture for several more hours, then DNA was prepared.

The plasmid DNA from the sub-pools was transfected into BHK 570 cells, and cell supernatants were collected and assayed as above. After approximately two hours, one sub-pool (#22) was scored as positive by microscopic examination (elongated cell shape). Several hours later two additional sub-pools (#19 and #28) were also scored positive. Remaining supernatants from each positive sub-pool were assayed against the control BaF3 cells and found to have no activity. In addition, the activity from the three positive sub-pools was found to be inhibited by the soluble Type I MPL receptor.

The replica plates from the three positive sub-pools were allowed to grow for several hours, then individual colonies were picked and used to innoculate 3-ml cultures. The cultures were grown approximately 8 hours at 37° C., then DNA was prepared by the miniprep method as described above. Plasmid DNA was transfected into BHK 570 cells, and supernatants were harvested approximately 10 hours later and assayed for activity. After one hour, one clone (designated T1081-19-215, corresponding to sub-pool #19) was scored positive. This clone was restreaked for single colonies. DNA was prepared from twelve colonies and transfected into BHK 570 cells. All twelve transfectants were later scored positive in the assay. DNA from one of the twelve positive colonies was transformed into *E. coli* DH5α. The plasmid was designated pZGmpl-1081. This transformant has been deposited with American Type Culture Collection, 12301 Parklawn Drive, Rockville, Md. under accession number 69566.

The nucleotide sequence of the cDNA encoding the hematopoietic protein was determined (SEQ ID NO: 1). Analysis of the encoded amino acid sequence (SEQ ID NO: 2) indicated that the amino terminus of the mature protein is at amino acid residue 45. Two methionine codons, at positions 105 and 174 of SEQ ID NO: 1, appear to be initiation codons, with the major site of initiation expected to be at position 174.

Example VIII

Hematopoietic Activity of Recombinant Protein

Marrow was harvested from femurs and tibias of a female CD-1 post-pregnant mouse into 25 ml of CATCH buffer (99 mg theophylline, 0.75 g sodium citrate, 75 mg adenosine, 20 ml Hank's balanced saline solution $Ca^{++}$ $Mg^{++}$-free, per 200 ml in $dH_2O$; pH 7.4). Cells were suspended into single cell suspension by pipeting with a 25 ml pipet. The volume was brought up to 50 ml with CATCH buffer, and the cells were pelleted at 1000 rpm for 7 minutes. The pellet was resuspended in 25 ml CATCH buffer and incubated in a T75 tissue culture flask for a first round of plastic adherence at 37° C. for 2 hours. Non-adherent cells were harvested by the addition of 15 ml of alpha-MEM+10% FBS (+L-glutamine, NaPyruvate, PSN) and washing non-adherent cells into suspension. The media and non-adherent cells were transfered into a 50 ml tube and centrifuged at 1000 rpm for 7 minutes to pellet cells. The pellet was resuspended in 25 ml CATCH buffer and incubated in a T75 flask for a second round of plastic adherence as described above for the first round. Following the final centrifugation and resuspension, the cells were counted. One-half ml of cells at 576,000 cells/ml was plated into 24-well tissue culture plates, together with sample media from control BHK cells or with conditioned media from BHK cells transfected with pZGmpl-1081. After three days incubation at 37° C., the cells were harvested and stained as described below.

One hundred fifty μl of cells were harvested from the control well treated with standard conditioned medium. 50 μl of cells were harvested from the well treated with conditioned medium from BHK cells transfected with pZGmpl-1081. These samples were cytospun and standard microscope slides were prepared.

The cytospin slides were fixed in 100% methanol. The slides were flooded with 1:1 Wright's (0.5 g Wright stain in 300 ml methanol)/$H_2O$ for 6 minutes, washed with water, and dried. Slides were then flooded with Geimsa stain (Sigma Chemical Corp.) in Sorensen buffer (2.28 g $KH_2PO_4$/2.38g $NaPO_4$ in 250 ml $H_2O$), washed with water, and dried.

After adjusting for the volumes used, the medium sample contained 120 megakaryocytes per 150 μl volume as compared to 9 megakaryocytes per 150 μl volume of control medium. In addition, these megakaryocytes in the treated experimental sample were observed microscopically to be significantly larger in size than control cells and to have significantly higher staining for polynuclei content.

Conditioned media from the mutant BaF3/MPLR1.1 line 24-11-5 #3 was collected in the absence of serum and concentrated 20-fold on a 10 Kd cut-off Amicon Inc. (Beverly, Mass.) filtration device. Marrow was harvested from mouse femurs and suspended in Iscove's Modified Dulbecco's medium+15% FCS. Following suspension, nucleated cells were counted and plated at 75,000 cells/ml with 0.9 ml/plate in semi-solid medium containing 50% methylcellulose, 15% FCS, 10% BSA, and 0.6% PSN in 1 ml tissue culture plates. Various conditioned medium and control samples were added to bring the total volume to 1 ml. Plates were incubated at 37° C./5% $CO_2$ for 6 days and then examined microscopically for counts of Granulocyte/Macrophage (GM) colonies. Plates incubated in the presence of the 24-11-5 #3 conditioned medium were observed to have weak GMCSF-like activity, producing a colony count of 25, compared with a count of zero for the negative control sample, and a count of 130 for a plate stimulated with a positive control (pokeweed mitogen spleen concentrated medium+erythropoietin).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. A method for obtaining cells that produce a ligand for an orphan growth factor receptor comprising:
    (a) providing parent cells, wherein growth of said parent cells is dependent upon an exogenous growth factor acting on said parent cells via a first growth factor receptor;
    (b) transfecting said parent cells with a DNA construct encoding an orphan growth factor receptor to produce transfected cells expressing said orphan growth factor receptor encoded by said DNA construct;
    (c) exposing said transfected cells to mutagenizing conditions to produce mutagenized cells;
    (d) culturing said mutagenized cells under conditions in which cell survival is dependent upon autocrine growth factor production;
    (e) recovering progeny cells that survive said culturing step; and
    (f) screening said progeny cells to identify cells that produce a ligand for said orphan growth factor receptor,
    wherein said first and orphan growth factor receptors are individually characterized by a polypeptide chain having a multi-domain structure comprising an extracellular ligand-binding domain, a single transmembrane domain, and an intracellular effector domain.

2. A method according to claim 1 wherein said screening step comprises assaying media conditioned by said progeny cells for growth-promoting activity on said transfected cells.

3. A method according to claim 2 wherein said screening step further comprises assaying media conditioned by said progeny cells for growth-promoting activity on said parent cells.

4. A method according to claim 1 wherein said screening step comprises culturing said progeny cells in the presence of an antibody to a known growth factor.

5. A method according to claim 1 wherein said screening step comprises assaying media conditioned by said progeny cells for growth-promoting activity on said transfected cells in the presence of an antibody to a known growth factor.

6. A method according to claim 1 wherein said screening step comprises culturing said progeny cells in the presence of a soluble form of said orphan growth factor receptor.

7. A method according to claim 1 wherein said screening step comprises assaying media conditioned by said progeny cells for growth-promoting activity on said transfected cells in the presence of a soluble form of said orphan growth factor receptor.

8. A method according to claim 1 wherein, prior to said culturing step, said mutagenized cells are cultured in the presence of said exogenous growth factor.

9. A method according to claim 1 wherein the parent cells do not express detectable levels of the orphan growth factor receptor.

10. A method according to claim 1 wherein said mutagenizing step comprises chemical treatment.

11. A method according to claim 1 wherein said parent cells are myeloid or lymphoid progenitor cells.

12. A method according to claim 1 wherein the effector domain of said first and orphan growth factor receptors is a protein kinase domain.

13. A method according to claim 1 wherein the extracellular ligand-binding domain of said first and orphan growth factor receptors comprises an immunoglobulin domain.

14. A method according to claim 1 wherein the extracellular ligand-binding domain of said first and orphan growth factor receptors comprises a hematopoietin domain.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
      ( A ) LENGTH: 1486 base pairs
      ( B ) TYPE: nucleic acid
      ( C ) STRANDEDNESS: double
      ( D ) TOPOLOGY: linear ( i i ) MOLECULE TYPE: cDNA ( v i i ) IMMEDIATE SOURCE:
      ( B ) CLONE: 1081.

( i x ) FEATURE:
      ( A ) NAME/KEY: CDS
      ( B ) LOCATION: 105..1241

( x i ) SEQUENCE DESCRIPTION: SEQ ID NO:1:

```
CCTCGTGCCG GTCCTGAGGC CCTTCTCCAC CCGGACAGAG TCCTTGGCCC ACCTCTCTCC              60

CACCCGACTC TGCCGAAAGA AGCACAGAAG CTCAAGCCGC CTCC ATG GCC CCA GGA             116
                                              Met Ala Pro Gly
                                               1

AAG ATT CAG GGG AGA GGC CCC ATA CAG GGA GCC ACT TCA GTT AGA CAC              164
Lys Ile Gln Gly Arg Gly Pro Ile Gln Gly Ala Thr Ser Val Arg His
 5              10              15              20

CTG GCC AGA ATG GAG CTG ACT GAT TTG CTC CTG GCG GCC ATG CTT CTT              212
Leu Ala Arg Met Glu Leu Thr Asp Leu Leu Leu Ala Ala Met Leu Leu
             25              30              35

GCA GTG GCA AGA CTA ACT CTG TCC AGC CCC GTA GCT CCT GCC TGT GAC              260
Ala Val Ala Arg Leu Thr Leu Ser Ser Pro Val Ala Pro Ala Cys Asp
         40              45              50

CCC AGA CTC CTA AAT AAA CTG CTG CGT GAC TCC CAC CTC CTT CAC AGC              308
Pro Arg Leu Leu Asn Lys Leu Leu Arg Asp Ser His Leu Leu His Ser
         55              60              65

CGA CTG AGT CAG TGT CCC GAC GTC GAC CCT TTG TCT ATC CCT GTT CTG              356
Arg Leu Ser Gln Cys Pro Asp Val Asp Pro Leu Ser Ile Pro Val Leu
     70              75              80

CTG CCT GCT GTG GAC TTT AGC CTG GGA GAA TGG AAA ACC CAG ACG GAA              404
Leu Pro Ala Val Asp Phe Ser Leu Gly Glu Trp Lys Thr Gln Thr Glu
 85              90              95             100

CAG AGC AAG GCA CAG GAC ATT CTA GGG GCA GTG TCC CTT CTA CTG GAG              452
Gln Ser Lys Ala Gln Asp Ile Leu Gly Ala Val Ser Leu Leu Leu Glu
             105             110             115

GGA GTG ATG GCA GCA CGA GGA CAG TTG GAA CCC TCC TGC CTC TCA TCC              500
Gly Val Met Ala Ala Arg Gly Gln Leu Glu Pro Ser Cys Leu Ser Ser
             120             125             130

CTC CTG GGA CAG CTT TCT GGG CAG GTT CGC CTC CTC TTG GGG GCC CTG              548
Leu Leu Gly Gln Leu Ser Gly Gln Val Arg Leu Leu Leu Gly Ala Leu
             135             140             145

CAG GGC CTC CTA GGA ACC CAG CTT CCT CTA CAG GGC AGG ACC ACA GCT              596
Gln Gly Leu Leu Gly Thr Gln Leu Pro Leu Gln Gly Arg Thr Thr Ala
     150             155             160
```

| | | | | | | | | | | | | | | | | |
|---|---|---|---|---|---|---|---|---|---|---|---|---|---|---|---|---|
| CAC | AAG | GAC | CCC | AAT | GCC | CTC | TTC | TTG | AGC | TTG | CAA | CAA | CTG | CTT | CGG | 644 |
| His 165 | Lys | Asp | Pro | Asn 170 | Ala | Leu | Phe | Leu | Ser 175 | Leu | Gln | Gln | Leu | Leu 180 | Arg | |
| GGA | AAG | GTG | CGC | TTC | CTG | CTT | CTG | GTA | GAA | GGT | CCC | ACC | CTC | TGT | GTC | 692 |
| Gly | Lys | Val | Arg | Phe 185 | Leu | Leu | Leu | Val | Glu 190 | Gly | Pro | Thr | Leu | Cys 195 | Val | |
| AGA | CGG | ACC | CTG | CCA | ACC | ACA | GCT | GTC | CCA | AGC | AGT | ACT | TCT | CAA | CTC | 740 |
| Arg | Arg | Thr | Leu 200 | Pro | Thr | Thr | Ala | Val 205 | Pro | Ser | Ser | Thr | Ser 210 | Gln | Leu | |
| CTC | ACA | CTA | AAC | AAG | TTC | CCA | AAC | AGG | ACT | TCT | GGA | TTG | TTG | GAG | ACG | 788 |
| Leu | Thr | Leu 215 | Asn | Lys | Phe | Pro | Asn 220 | Arg | Thr | Ser | Gly | Leu 225 | Leu | Glu | Thr | |
| AAC | TTC | AGT | GTC | ACA | GCC | AGA | ACT | GCT | GGC | CCT | GGA | CTT | CTG | AGC | AGG | 836 |
| Asn | Phe 230 | Ser | Val | Thr | Ala | Arg 235 | Thr | Ala | Gly | Pro | Gly 240 | Leu | Leu | Ser | Arg | |
| CTT | CAG | GGA | TTC | AGA | GTC | AAG | ATT | ACT | CCT | GGT | CAG | CTA | AAT | CAA | ACC | 884 |
| Leu 245 | Gln | Gly | Phe | Arg | Val 250 | Lys | Ile | Thr | Pro | Gly 255 | Gln | Leu | Asn | Gln | Thr 260 | |
| TCC | AGG | TCC | CCA | GTC | CAA | ATC | TCT | GGA | TAC | CTG | AAC | AGG | ACA | CAC | GGA | 932 |
| Ser | Arg | Ser | Pro | Val 265 | Gln | Ile | Ser | Gly | Tyr 270 | Leu | Asn | Arg | Thr | His 275 | Gly | |
| CCT | GTG | AAT | GGA | ACT | CAT | GGG | CTC | TTT | GCT | GGA | ACC | TCA | CTT | CAG | ACC | 980 |
| Pro | Val | Asn | Gly 280 | Thr | His | Gly | Leu | Phe 285 | Ala | Gly | Thr | Ser | Leu 290 | Gln | Thr | |
| CTG | GAA | GCC | TCA | GAC | ATC | TCG | CCC | GGA | GCT | TTC | AAC | AAA | GGC | TCC | CTG | 1028 |
| Leu | Glu | Ala 295 | Ser | Asp | Ile | Ser | Pro 300 | Gly | Ala | Phe | Asn | Lys 305 | Gly | Ser | Leu | |
| GCA | TTC | AAC | CTC | CAG | GGT | GGA | CTT | CCT | CCT | TCT | CCA | AGC | CTT | GCT | CCT | 1076 |
| Ala | Phe 310 | Asn | Leu | Gln | Gly | Gly 315 | Leu | Pro | Pro | Ser | Pro 320 | Ser | Leu | Ala | Pro | |
| GAT | GGA | CAC | ACA | CCC | TTC | CCT | CCT | TCA | CCT | GCC | TTG | CCC | ACC | ACC | CAT | 1124 |
| Asp | Gly 325 | His | Thr | Pro | Phe 330 | Pro | Pro | Ser | Pro | Ala 335 | Leu | Pro | Thr | Thr | His 340 | |
| GGA | TCT | CCA | CCC | CAG | CTC | CAC | CCC | CTG | TTT | CCT | GAC | CCT | TCC | ACC | ACC | 1172 |
| Gly | Ser | Pro | Pro | Gln 345 | Leu | His | Pro | Leu | Phe 350 | Pro | Asp | Pro | Ser | Thr 355 | Thr | |
| ATG | CCT | AAC | TCT | ACC | GCC | CCT | CAT | CCA | GTC | ACA | ATG | TAC | CCT | CAT | CCC | 1220 |
| Met | Pro | Asn | Ser 360 | Thr | Ala | Pro | His | Pro 365 | Val | Thr | Met | Tyr | Pro 370 | His | Pro | |
| AGG | AAT | TTG | TCT | CAG | GAA | ACA | TAGCGCGGGC | ACTGGCCCAG | TGAGCGTCTG | | | | | | | 1271 |
| Arg | Asn | Leu | Ser 375 | Gln | Glu | Thr | | | | | | | | | | |

```
CAGCTTCTCT CGGGGACAAG CTTCCCCAGG AAGGCTGAGA GGCAGCTGCA TCTGCTCCAG    1331
ATGTTCTGCT TTCACCTAAA AGGCCCTGGG GAAGGGATAC ACAGCACTGG AGATTGTAAA    1391
ATTTTAGGAG CTATTTTTTT TTAACCTATC AGCAATATTC ATCAGAGCAG CTAGCGATCT    1451
TTGGTCTATT TTCGGTATAA ATTTGAAAAT CACTA                               1486
```

( 2 ) INFORMATION FOR SEQ ID NO:2:

( i ) SEQUENCE CHARACTERISTICS:
        ( A ) LENGTH: 379 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Pro Gly Lys Ile Gln Gly Arg Gly Pro Ile Gln Gly Ala Thr
 1           5                  10                  15
```

```
Ser  Val  Arg  His  Leu  Ala  Arg  Met  Glu  Leu  Thr  Asp  Leu  Leu  Leu  Ala
               20                  25                  30

Ala  Met  Leu  Leu  Ala  Val  Ala  Arg  Leu  Thr  Leu  Ser  Ser  Pro  Val  Ala
          35                  40                       45

Pro  Ala  Cys  Asp  Pro  Arg  Leu  Leu  Asn  Lys  Leu  Leu  Arg  Asp  Ser  His
     50                       55                  60

Leu  Leu  His  Ser  Arg  Leu  Ser  Gln  Cys  Pro  Asp  Val  Asp  Pro  Leu  Ser
65                       70                  75                            80

Ile  Pro  Val  Leu  Leu  Pro  Ala  Val  Asp  Phe  Ser  Leu  Gly  Glu  Trp  Lys
                    85                       90                       95

Thr  Gln  Thr  Glu  Gln  Ser  Lys  Ala  Gln  Asp  Ile  Leu  Gly  Ala  Val  Ser
               100                 105                      110

Leu  Leu  Leu  Glu  Gly  Val  Met  Ala  Ala  Arg  Gly  Gln  Leu  Glu  Pro  Ser
          115                      120                      125

Cys  Leu  Ser  Ser  Leu  Leu  Gly  Gln  Leu  Ser  Gly  Gln  Val  Arg  Leu  Leu
     130                      135                      140

Leu  Gly  Ala  Leu  Gln  Gly  Leu  Leu  Gly  Thr  Gln  Leu  Pro  Leu  Gln  Gly
145                      150                 155                           160

Arg  Thr  Thr  Ala  His  Lys  Asp  Pro  Asn  Ala  Leu  Phe  Leu  Ser  Leu  Gln
                    165                      170                 175

Gln  Leu  Leu  Arg  Gly  Lys  Val  Arg  Phe  Leu  Leu  Leu  Val  Glu  Gly  Pro
               180                 185                      190

Thr  Leu  Cys  Val  Arg  Arg  Thr  Leu  Pro  Thr  Thr  Ala  Val  Pro  Ser  Ser
          195                      200                 205

Thr  Ser  Gln  Leu  Leu  Thr  Leu  Asn  Lys  Phe  Pro  Asn  Arg  Thr  Ser  Gly
     210                      215                 220

Leu  Leu  Glu  Thr  Asn  Phe  Ser  Val  Thr  Ala  Arg  Thr  Ala  Gly  Pro  Gly
225                           230                 235                      240

Leu  Leu  Ser  Arg  Leu  Gln  Gly  Phe  Arg  Val  Lys  Ile  Thr  Pro  Gly  Gln
               245                      250                      255

Leu  Asn  Gln  Thr  Ser  Arg  Ser  Pro  Val  Gln  Ile  Ser  Gly  Tyr  Leu  Asn
               260                      265                 270

Arg  Thr  His  Gly  Pro  Val  Asn  Gly  Thr  His  Gly  Leu  Phe  Ala  Gly  Thr
          275                      280                 285

Ser  Leu  Gln  Thr  Leu  Glu  Ala  Ser  Asp  Ile  Ser  Pro  Gly  Ala  Phe  Asn
     290                      295                      300

Lys  Gly  Ser  Leu  Ala  Phe  Asn  Leu  Gln  Gly  Gly  Leu  Pro  Pro  Ser  Pro
305                      310                      315                      320

Ser  Leu  Ala  Pro  Asp  Gly  His  Thr  Pro  Phe  Pro  Pro  Ser  Pro  Ala  Leu
               325                      330                      335

Pro  Thr  Thr  His  Gly  Ser  Pro  Pro  Gln  Leu  His  Pro  Leu  Phe  Pro  Asp
               340                      345                 350

Pro  Ser  Thr  Thr  Met  Pro  Asn  Ser  Thr  Ala  Pro  His  Pro  Val  Thr  Met
          355                      360                 365

Tyr  Pro  His  Pro  Arg  Asn  Leu  Ser  Gln  Glu  Thr
     370                 375
```

( 2 ) INFORMATION FOR SEQ ID NO:3:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc5499

( x i ) SEQUENCE DESCRIPTION: SEQ ID NO:3:

CGAGCCACTT TCTGCACTCC TCGAGTTTTT TTTTTTTTTT TT                                42

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc5746

( x i ) SEQUENCE DESCRIPTION: SEQ ID NO:4:

GAGAGAGAGA GAGAATTCAT GCCCTCCTGG GCCCTCTTCA TGGTC                             45

( 2 ) INFORMATION FOR SEQ ID NO:5:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc5762

( x i ) SEQUENCE DESCRIPTION: SEQ ID NO:5:

AGAGAGAGAG AGAGCTCGAG TCAAGGCTGC TGCCAATAGC TTAGTGGTAG GT                     52

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc5742

( x i ) SEQUENCE DESCRIPTION: SEQ ID NO:6:

GACCCTGGAG CTGCGCCCGC GATCTCGCTA                                              30

( 2 ) INFORMATION FOR SEQ ID NO:7:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6091

( x i ) SEQUENCE DESCRIPTION: SEQ ID NO:7:

GAGCACAGAA TTCACTACTC GAGGCGGCCG CTTTTTTTTT TTTTTTTTT                         49

( 2 ) INFORMATION FOR SEQ ID NO:8:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6603

( x i ) SEQUENCE DESCRIPTION: SEQ ID NO:8:

GAGGAATTCG CAGAAGCCAT GCCCTCTTGG GCCCTCTTCA TGGTC 45

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:9:

Val Arg Thr Ser Pro Ala Gly Glu
1               5

( 2 ) INFORMATION FOR SEQ ID NO:10:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6704

( x i ) SEQUENCE DESCRIPTION: SEQ ID NO:10:

GAAGAGGAAT TCACCATGGA TGTCTTCTTG CTGGCCTTGG GCACAGAG 48

( 2 ) INFORMATION FOR SEQ ID NO:11:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6703

( x i ) SEQUENCE DESCRIPTION: SEQ ID NO:11:

CGACTTTACC TCGAGTGCTA CTGATGCTCT TCTGCCAGCA GTCTCGGAGC CCGTGGACAC 60

( 2 ) INFORMATION FOR SEQ ID NO:12:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6707

( x i ) SEQUENCE DESCRIPTION: SEQ ID NO:12:

AATTCGCCAT GGGACTCGAG CATCACCATC ACCATCACTG AG 42

( 2 ) INFORMATION FOR SEQ ID NO:13:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6706

( x i ) SEQUENCE DESCRIPTION: SEQ ID NO:13:

```
GATCCTCAGT GATGGTGATG GTGATGCTCG AGTCCCATGG CG                              42
```

( 2 ) INFORMATION FOR SEQ ID NO:14:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6172

( x i ) SEQUENCE DESCRIPTION: SEQ ID NO:14:

```
GTCGGTGCTC AGCATTCACT ACTCGAGGGT TTTTTTTTT TTTTTTT                          47
```

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6936

( x i ) SEQUENCE DESCRIPTION: SEQ ID NO:15:

```
AATTGGCGGC CGCGTCGACT CGTGGATG                                              28
```

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6937

( x i ) SEQUENCE DESCRIPTION: SEQ ID NO:16:

```
AATTCATCCA CGAGTCGACG CGGCCGCC                                              28
```

( 2 ) INFORMATION FOR SEQ ID NO:17:

( i ) SEQUENCE CHARACTERISTICS:
        ( A ) LENGTH: 633 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met Pro Ser Trp Ala Leu Phe Met Val Thr Ser Cys Leu Leu Ala
 1               5                  10                  15

Leu Pro Asn Gln Ala Gln Val Thr Ser Gln Asp Val Phe Leu Leu Ala
            20                  25                  30

Leu Gly Thr Glu Pro Leu Asn Cys Phe Ser Gln Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Arg Gly Glu Lys Pro Arg Ala Cys Pro Leu Tyr
65                  70                  75                  80

Ser Gln Ser Val Pro Thr Phe Gly Thr Arg Tyr Val Cys Gln Phe Pro
                    85                  90                  95
```

-continued

| | | | | | | | | | | | | | | |
|---|---|---|---|---|---|---|---|---|---|---|---|---|---|---|
| Ala | Gln | Asp | Glu 100 | Val | Arg | Leu | Phe | Phe 105 | Pro | Leu | His | Leu 110 | Trp | Val | Lys |
| Asn | Val | Ser 115 | Leu | Asn | Gln | Thr 120 | Leu | Ile | Gln | Arg | Val 125 | Leu | Phe | Val | Asp |
| Ser | Val 130 | Gly | Leu | Pro | Ala 135 | Pro | Arg | Val | Ile | Lys 140 | Ala | Arg | Gly | Gly |
| Ser 145 | Gln | Pro | Gly | Glu 150 | Leu | Gln | Ile | His | Trp 155 | Glu | Ala | Pro | Ala | Pro 160 | Glu |
| Ile | Ser | Asp | Phe | Leu 165 | Arg | His | Glu | Leu | Arg 170 | Tyr | Gly | Pro | Thr | Asp 175 | Ser |
| Ser | Asn | Ala | Thr 180 | Ala | Pro | Ser | Val | Ile 185 | Gln | Leu | Leu | Ser | Thr 190 | Glu | Thr |
| Cys | Cys | Pro 195 | Thr | Leu | Trp | Met | Pro 200 | Asn | Pro | Val | Pro | Val 205 | Leu | Asp | Gln |
| Pro | Pro 210 | Cys | Val | His | Pro | Thr 215 | Ala | Ser | Gln | Pro | His 220 | Gly | Pro | Val | Arg |
| Thr 225 | Ser | Pro | Ala | Gly | Glu 230 | Ala | Pro | Phe | Leu | Thr 235 | Val | Lys | Gly | Gly | Ser 240 |
| Cys | Leu | Val | Ser | Gly 245 | Leu | Gln | Ala | Gly | Lys 250 | Ser | Tyr | Trp | Leu | Gln 255 | Leu |
| Arg | Ser | Gln | Pro 260 | Asp | Gly | Val | Ser | Leu 265 | Arg | Gly | Ser | Trp | Gly 270 | Pro | Trp |
| Ser | Phe | Pro 275 | Val | Thr | Val | Asp | Leu 280 | Pro | Gly | Asp | Ala | Val 285 | Thr | Ile | Gly |
| Leu | Gln 290 | Cys | Phe | Thr | Leu | Asp 295 | Leu | Lys | Met | Val | Thr 300 | Cys | Gln | Trp | Gln |
| Gln 305 | Gln | Asp | Arg | Thr | Ser 310 | Ser | Gln | Gly | Phe | Phe 315 | Arg | His | Ser | Arg | Thr 320 |
| Arg | Cys | Cys | Pro | Thr 325 | Asp | Arg | Asp | Pro | Thr 330 | Trp | Glu | Lys | Cys | Glu 335 | Glu |
| Glu | Glu | Pro | Arg 340 | Pro | Gly | Ser | Gln | Pro 345 | Ala | Leu | Val | Ser | Arg 350 | Cys | His |
| Phe | Lys | Ser 355 | Arg | Asn | Asp | Ser | Val 360 | Ile | His | Ile | Leu | Val 365 | Glu | Val | Thr |
| Thr | Ala 370 | Gln | Gly | Ala | Val | His 375 | Ser | Tyr | Leu | Gly | Ser 380 | Pro | Phe | Trp | Ile |
| His 385 | Gln | Ala | Val | Leu | Leu 390 | Pro | Thr | Pro | Ser | Leu 395 | His | Trp | Arg | Glu | Val 400 |
| Ser | Ser | Gly | Arg | Leu 405 | Glu | Leu | Glu | Trp | Gln 410 | His | Gln | Ser | Ser | Trp 415 | Ala |
| Ala | Gln | Glu | Thr 420 | Cys | Tyr | Gln | Leu | Arg 425 | Tyr | Thr | Gly | Glu | Gly 430 | Arg | Glu |
| Asp | Trp | Lys 435 | Val | Leu | Glu | Pro | Ser 440 | Leu | Gly | Ala | Arg | Gly 445 | Gly | Thr | Leu |
| Glu | Leu 450 | Arg | Pro | Arg | Ala | Arg 455 | Tyr | Ser | Leu | Gln | Leu 460 | Arg | Ala | Arg | Leu |
| Asn 465 | Gly | Pro | Thr | Tyr | Gln 470 | Gly | Pro | Trp | Ser | Ala 475 | Trp | Ser | Pro | Pro | Ala 480 |
| Arg | Val | Ser | Thr | Gly 485 | Ser | Glu | Thr | Ala | Trp 490 | Ile | Thr | Leu | Val | Thr 495 | Ala |
| Leu | Leu | Leu | Val 500 | Leu | Ser | Leu | Ser | Ala 505 | Leu | Leu | Gly | Leu | Leu 510 | Leu | Leu |
| Lys | Trp | Gln 515 | Phe | Pro | Ala | His | Tyr 520 | Arg | Arg | Leu | Arg | His 525 | Ala | Leu | Trp |

| | | | | | | | | | | | | | |
|---|---|---|---|---|---|---|---|---|---|---|---|---|---|
| Pro | Ser 530 | Leu | Pro | Asp | Leu | His 535 | Arg | Val | Leu | Gly | Gln 540 | Tyr | Leu | Arg | Asp |
| Thr 545 | Ala | Ala | Leu | Ser | Pro 550 | Ser | Lys | Ala | Thr | Val 555 | Thr | Asp | Ser | Cys | Glu 560 |
| Glu | Val | Glu | Pro | Ser 565 | Leu | Leu | Glu | Ile | Leu 570 | Pro | Lys | Ser | Ser | Glu 575 | Ser |
| Thr | Pro | Leu | Pro 580 | Leu | Cys | Pro | Ser | Gln 585 | Pro | Gln | Met | Asp | Tyr 590 | Arg | Gly |
| Leu | Gln | Pro 595 | Cys | Leu | Arg | Thr | Met 600 | Pro | Leu | Ser | Val | Cys 605 | Pro | Pro | Met |
| Ala | Glu 610 | Thr | Gly | Ser | Cys | Cys 615 | Thr | Thr | His | Ile | Ala 620 | Asn | His | Ser | Tyr |
| Leu 625 | Pro | Leu | Ser | Tyr | Trp 630 | Gln | Gln | Pro | | | | | | | |